United States Patent
Wirth et al.

(10) Patent No.: US 10,898,312 B2
(45) Date of Patent: Jan. 26, 2021

(54) TISSUE GRAFTS WITH FENESTRATIONS

(71) Applicant: The Regents of the University of California, Oakland, CA (US)

(72) Inventors: Garrett A. Wirth, Irvine, CA (US); Keyianoosh Z. Paydar, Irvine, CA (US); Patrick Guidotti, Irvine, CA (US); Donald S. Mowlds, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 159 days.

(21) Appl. No.: 15/032,567

(22) PCT Filed: Oct. 27, 2014

(86) PCT No.: PCT/US2014/062466
§ 371 (c)(1),
(2) Date: Apr. 27, 2016

(87) PCT Pub. No.: WO2015/065923
PCT Pub. Date: May 7, 2015

(65) Prior Publication Data
US 2016/0256259 A1    Sep. 8, 2016

Related U.S. Application Data

(60) Provisional application No. 61/896,551, filed on Oct. 28, 2013.

(51) Int. Cl.
*A61F 2/12*    (2006.01)
*A61F 2/00*    (2006.01)
*A61L 27/36*   (2006.01)

(52) U.S. Cl.
CPC .............. *A61F 2/12* (2013.01); *A61F 2/0063* (2013.01); *A61L 27/3633* (2013.01);
(Continued)

(58) Field of Classification Search
CPC .. A61F 2/12; A61F 2/0063; A61F 2002/0068; A61F 2250/0018;
(Continued)

(56) References Cited

U.S. PATENT DOCUMENTS

| 8,049,059 B2 | 11/2011 | Bleyer et al. |
| 2004/0260315 A1 | 12/2004 | Dell et al. |

(Continued)

FOREIGN PATENT DOCUMENTS

WO    WO-2013/106556 A2    7/2013

OTHER PUBLICATIONS

International Search Report and Written Opinion (ISR/WO) for International Application No. PCT/US2014/062466, dated Mar. 24, 2015.
(Continued)

*Primary Examiner* — Jerrah Edwards
*Assistant Examiner* — Rokhaya Diop
(74) *Attorney, Agent, or Firm* — Foley & Lardner LLP

(57) ABSTRACT

Fenestrated tissue grafts and acellular dermal matrices (ADMs) for use, for example, in breast reconstruction, are disclosed herein. In various embodiments, the improved tissue grafts are used in two-stage tissue expander breast reconstruction. Disclosed embodiments include altered ADMs and other tissue grafts, which comprise strategically placed fenestrations, and methods of making the same. The addition of specific patterns of fenestrations in the graft improve the breast reconstructive experience by increasing intra-operative fill volume and decreasing time to full expansion; such alterations to the graft may also increase cosmetic outcomes and patient comfort. In some embodiments, particular lengths, shapes, and measurements of overlap are used in the fenestration pattern.

21 Claims, 14 Drawing Sheets

(52) U.S. Cl.
CPC ............... *A61F 2230/0019* (2013.01); *A61F 2250/0018* (2013.01); *A61L 27/36* (2013.01); *A61L 2430/04* (2013.01)

(58) Field of Classification Search
CPC ............. A61F 2230/0019; A61F 2/105; A61L 27/3633; A61L 27/36; A61L 2430/04
See application file for complete search history.

(56) References Cited

U.S. PATENT DOCUMENTS

| | | | |
|---|---|---|---|
| 2006/0141012 A1* | 6/2006 | Gingras | A61F 2/08 424/442 |
| 2008/0097601 A1* | 4/2008 | Codori-Hurff | A61F 2/12 623/8 |
| 2009/0125107 A1 | 5/2009 | Maxwell | |
| 2011/0022171 A1* | 1/2011 | Richter | A61F 2/12 623/8 |
| 2011/0262515 A1 | 10/2011 | Lauritzen et al. | |
| 2012/0143329 A1 | 6/2012 | Kim | |
| 2013/0085579 A1* | 4/2013 | Markman | A61F 2/062 623/23.72 |
| 2015/0157451 A1 | 6/2015 | Bowley et al. | |
| 2015/0250582 A1 | 9/2015 | Greenhalgh et al. | |
| 2016/0256259 A1 | 9/2016 | Wirth et al. | |
| 2016/0331504 A1 | 11/2016 | Wang et al. | |
| 2017/0340437 A1* | 11/2017 | Bowley | A61L 27/3695 |
| 2017/0367807 A1 | 12/2017 | Chen et al. | |
| 2018/0055624 A1 | 3/2018 | Barere et al. | |

OTHER PUBLICATIONS

Extended European Search Report dated Jul. 8, 2017, from application No. 14858603.5.
Artz, et al., "Breast reconstruction with a subcutaneous tissue expander followed with a polyurethanecovered silicone breast implant," Annals of Plastic Surgery, vol. 20, issue 6, pp. 517-521 (Jun. 1988).
Becker, et al., "Immediate implant-based prepectoral breast reconstruction using a vertical incision," PRS Global Open, vol. 3(6), e412, 9 pages (Jun. 2015).
Bernini, et al., "Subcutaneous direct-toimplant breast reconstruction: surgical, functional, and aesthetic results after long-term follow-up," PRS Global Open, vol. 3(12), e574, 9 pages (Dec. 2015).
Caputo, et al., "Skin-reduction breast reconstructions with prepectoral implant," Plastic and Reconstructive Surgery, vol. 137, issue 6, pp. 1702-1705 (Jun. 2016).
Casella, et al., "TiLoop(R) Bra mesh used for immediate breast reconstruction: comparison of retropectoral and subcutaneous implant placement in a prospective single-institution series," European Journal of Plastic Surgery, vol. 37, issue 11, pp. 599-604 (Nov. 2014).
Cheng, et al., "Treatment of Capsular Contracture Using Complete Implant Coverage by Acellular Dermal Matrix: A Novel Technique," Plastic and Reconstructive Surgery, vol. 132, issue 3, pp. 519-529 (Sep. 2013).
Downs & Hedges, "An alternative technique for immediate direct-to-implant breast reconstruction a case series," PRS Global Open, vol. 4(7), e821, 8 pages (Jul. 2016).

Engel, et al., "Subcutaneous tissue expansion and subsequent subpectoral implantation for breast reconstruction in Asian patients: safety and outcome," Annals of Plastic Surgery, vol. 70, issue 2, pp. 135-143 (Feb. 2013).
Gruber, et al., "Breast reconstruction following mastectomy: a comparison of submuscular and subcutaneous techniques," Plastic and Reconstructive Surgery, vol. 67, issue 3, pp. 312-317 (Mar. 1981).
Guthrie, "Breast reconstruction after radical mastectomy," Plastic and Reconstructive Surgery, vol. 57, issue 1, pp. 14-22 (Jan. 1976).
Iqbal, et al., "Host integration of an acellular dermal matrix: Braxon mesh in breast reconstruction," Clinical Breast Cancer, vol. 16, issue 6, pp. e209-e211 (Dec. 2016).
Kim, et al., "A meta-analysis of human acellular dermis and submuscular tissue expander breast reconstruction," Plastic and Reconstructive Surgery, vol. 129, issue 1, pp. 28-41, (Jan. 2012).
Krishnan, et al., "Is Single-Stage Prosthetic Reconstruction Cost Effective? A Cost-Utility Analysis for the Use of Direct-to-Implant Breast Reconstruction Relative to Expander-Implant Reconstruction in Postmastectomy Patients," Plastic and Reconstructive Surgery, vol. 138, issue 3, pp. 537-547 (Sep. 2016).
Martin, et al., "Use of Fenestrations in Acellular Dermal Allograft in Two-Stage Tissue Expander/Implant Breast Reconstruction," Plastic and Reconstructive Surgery, vol. 134, issue 5, pp. 901-904 (Nov. 2014).
Mowlds, et al., "Capsular contracture in implant-based breast reconstruction: examining the role of acellular dermal matrix fenestrations," Plastic and Reconstructive Surgery, vol. 136, issue 4, pp. 629-635 (Oct. 2015).
Palaia, et al., "Incidence of seromas and infections using fenestrated versus nonfenestrated acellular dermal matrix in breast reconstructions," PRS Global Open, vol. 3(11), e569, 7 pages (Nov. 2015).
Radovan, "Breast reconstruction after mastectomy using the temporary expander," Plastic and Reconstructive Surgery, vol. 69, issue 2, pp. 195-208 (Feb. 1982).
Reitsamer & Peintinger, "Prepectoral implant placement and complete coverage with porcine acellular dermal matrix: a new technique for direct-to-implant breast reconstruction after nipple-sparing mastectomy," Journal of Reconstructive and Aesthetic Surgery, vol. 68, issue 2, pp. 162-167 (Feb. 2015).
Salibian, et al., "Staged suprapectoral expander/implant reconstruction without acellular dermal matrix following nipple-sparing mastectomy," Plastic and Reconstructive Surgery, vol. 139, issue 1, pp. 30-39 (Jan. 2017).
Salibian, et al., "Subcutaneous implant-based breast reconstruction with acellular dermal matrix/mesh: a systematic review," PRS Global Open, vol. 4(11), e1139, 8 pages (Nov. 2016).
Schnarrs, et al., "Complication Rates With Human Acellular Dermal Matrices: Retrospective Review of 211 Consecutive Breast Reconstructions," PRS Global Open, vol. 4(11), e1118, 9 pages (Nov. 2016).
Sigalove, et al., "Prepectoral implantbased breast reconstruction: rationale, indications, and preliminary results," Plastic and Reconstructive Surgery, vol. 139, issue 2, pp. 287-294 (Feb. 2017).
Wirth, et al., "Acellular dermal matrix fenestrations and their effect on breast shape," European Journal of Plastic Surgery, vol. 38, issue 4, pp. 267-272 (Aug. 2015).
Zhu, et al., "Comparison of subcutaneous versus submuscular expander placement in the first stage of immediate breast reconstruction," Journal of Reconstructive and Aesthetic Surgery, vol. 69, issue 4, pp. e77-e86 (Apr. 2016).
International Search Report and Written Opinion dated Jul. 10, 2018, for application No. PCT/US2018/028644.

* cited by examiner

TISSUE GRAFTS WITH FENESTRATIONS

CROSS-REFERENCE TO RELATED APPLICATIONS

The present application is a national stage entry under 35 U.S.C. § 371 of International Application No. PCT/US2014/062466, filed Oct. 27, 2014, which claims the benefit of U.S. Provisional Application No. 61/896,551, filed Oct. 28, 2013, the disclosure of each of which is herein expressly incorporated by reference in its entirety.

FIELD

The present technology relates generally to the field of biomaterials and specifically to improved graft materials for use in surgical procedures.

BACKGROUND

Throughout this disclosure, various technical and patent publications are referenced to more fully describe the state of the relevant art. The full bibliographic information for these publications referenced by an Arabic number can be found listed at the end of the specification, immediately preceding the claims. All listed publications and those noted within the present specification are herein incorporated by reference, in their entirety.

In 2011, over 69,000 two-stage tissue expander and implant breast reconstructions were documented by the American Society of Plastic Surgery, accounting for 70% of total breast reconstructions in the United States[1]. The use of acellular dermal matrices (ADMs), also referred to as acellular tissue matrices (ATM), has become increasingly prevalent in primary (direct-to-implant) and staged breast reconstructions over the last several years[10]. ADMs can be derived from cadaveric dermis and can be composed primarily of extracellular matrix (ECM) components, which provide a scaffold upon which resident cells can migrate following implantation, facilitating matrix integration[11]. ADMs serve several functions when utilized in breast reconstruction. Most notably, they facilitate greater soft tissue coverage and implant or tissue expander suspension within a post-mastectomy tissue pocket that may allow for direct-to-implant reconstruction[12, 13] and a decrease in the time to complete expansion in two-stage reconstructions[14].

In 2005, Breuing et al. was the first to describe the use of ADMs in breast reconstruction[20], whereby the ADM acted as an expandable sling supporting the inferior and lateral aspects of the implant or tissue expander providing regenerative tissue coverage. Several factors contribute to the final position of the implant after it settles onto the ADM: the elastic properties of the matrix, the ADM's position on the chest wall, and the weight of the implant. Together with the shape, size and projection of the breast implant, these variables act in concert to define the expansion and projection of the inferior pole of the breast following implantation.

However, despite widespread use, concerns still exist regarding the use of ADM, including risk of infection, presence of an inflammatory reaction, risks of seroma formation, and increased cost. Complications in ADM-assisted breast reconstruction are comparable to non-ADM reconstructions[10], and higher rates of seromas have been associated with ADM-assisted reconstructions[24-27]. Additionally, a recent study comparing two-stage breast reconstruction using a standard, traditional sub-muscular pocket to reconstruction using an ADM as an inferior-lateral sling did not find a significant difference in the rate of post-operative expansion[5].

Thus, a need still exists for an improved graft for breast reconstruction that decreases the risks of infection and seroma formation, decreases costs, and improves cosmetic outcomes. A need similarly exists for an improved graft that decreases the risks of infection and seroma formation, decreases costs, and improves cosmetic outcomes in a wide variety of applications. For example, a need exists for improved grafts for use in abdominal hernia repairs, buttocks augmentation procedures, chest wall reconstructions, scalp reconstructions, and various skin and soft tissue grafting procedures.

SUMMARY

Various embodiments disclosed herein are directed to improved tissue grafts having patterns of fenestrations disposed therein, which may fulfill one or more of the needs described above. For example, one or more of the provided embodiments may result in reduced risk of infection, reduced risk of seroma formation, decreased costs, and/or improved cosmetic outcomes in comparison to existing graft materials. Various embodiments provided herein describe improved grafts, used, for example, for treatment following severe trauma, surgery, burns, infections, or cancer to the skin; the embodiments may also be applicable to other grafts, such as, for example, fat grafts or other engineered scaffolds. In some embodiments, the described fenestrated tissue grafts are acellular dermal matrices (ADMs); in other embodiments, the fenestrated tissue grafts may be formed of any other suitable tissue graft, such as, for example, a synthetic dermal regeneration system (e.g., Integra® developed by Integra LifeSciences Corporation) or other synthetic graft, an autograft, an allograft, or a xenograft.

One aspect of the disclosure relates to a tissue graft modified for more successful incorporation of the graft into surrounding tissue. In various embodiments, the modification includes adding fenestrations to the graft to achieve improved patient outcomes (e.g., lower risks of fluid collection, improved aesthetic appearance, faster incorporation into the tissue, etc.). Furthermore, in various embodiments, the modification includes the addition of small alignment perforations, which increases operative efficiency and aesthetic outcome by improving product placement and alignment.

In some embodiments, the tissue graft is an ADM configured for use in breast reconstruction. In such an embodiment, the added fenestrations improve aesthetic results by allowing for increased inferior pole expansion with preservation of the natural inframammary fold (IMF) and shape. This also decreases seroma formation by reducing potential "dead-space", also known as "potential space" (due to increased tissue expander size or final implant placement) and by providing better drainage of the breast pocket with a single drain. Specifically, the increased effacement between the implant and the fenestrated ADM results in increased incorporation of the material by surrounding tissue. In some embodiments, the disclosed fenestration patterns, organized symmetrically and/or asymmetrically, are applied to the most common size of ADM currently used clinically; in other embodiments, the fenestration patterns are applied to newer shaped ADM samples.

Another aspect disclosed herein is a method for successful incorporation of the ADM in tissue reconstruction, such as breast reconstruction, using fenestrations. In some embodiments, the method includes performing an ADM-assisted breast reconstruction, wherein the ADM includes alignment perforations to aid in ADM placement, and wherein the ADM also includes a pattern of fenestrations, for example, any pattern of fenestrations described elsewhere herein. Application of ADM having strategically-placed fenestrations with proper overlap, as provided in various embodiments, improves aesthetic results by allowing for increased inferior pole expansion with preservation of the natural IMF and shape. This also decreases seroma formation by reducing potential "dead-space" and providing better drainage of the breast pocket with a single drain in the subcutaneous space. Infectious complications are reduced with faster incorporation of the ADM due to improved vascular ingrowth owing to product thinning due to greater immediate expansion and better abutment of the product to subcutaneous tissue, which contains the blood supply required for proper product integration. Faster incorporation is also made possible by the intra-graft spread of vascular ingrowth stemming from the fenestrations, where host's cells (e.g., stem cell/fat grafted and/or native breast's subcutaneous or subdermal tissue) immediately populate, thus adding another dimension to the product integration.

A mathematical model is disclosed herein to describe these modifications to the graft used in breast reconstruction and elucidate the mechanism behind their effect on breast shape.

The advantages of the various apparatus, system, and method embodiments disclosed herein are multiple. By utilizing fenestrations described herein, the coverage achieved by a graft can be increased, allowing surgeons to utilize a smaller piece of graft when compared to a non-fenestrated material. This decreases costs to the manufacturer, surgeons, and ultimately, patients. It also allows the manufacturer to increase the number of individual graft units it can procure, treat, package, and sell. Additionally, the disclosed fenestrated product with alignment perforations makes surgery more efficient, reducing anesthesia time and its related risks and decreasing the need for revisional operations in the future. Furthermore, with the use of fenestrations and alignment perforations, the inset is faster, fewer drains are required and more accurate product alignment is possible. This improves the aesthetic and safety profile while simultaneously decreasing postoperative complications such as seroma formation and infection, owing to faster product incorporation with ADM thinning and allowing for intra-graft vascular ingrowth. Additionally, it optimizes product to breast flap approximation when the alignment perforations are placed within grafts configured for breast reconstructions. The addition of fenestrations in such grafts also facilitates improved graft effacement with the breast flap, decreasing the risk of loss, non-incorporation, and infection as well as increasing the benefit of earlier and more efficient incorporation of the graft. Furthermore, as shown clinically, there are other benefits of using the graft modifications described herein with tissue expanders and breast reconstruction, including greater "on-table" fill and improved inferior breast pole expansion, which ultimately leads to fewer post-operative expansions and office visits, improved patient satisfaction, and optimal aesthetic outcomes.

The foregoing is a summary and necessarily contains generalizations, simplifications, and omissions of detail. The summary is not intended in any way to be limiting, and those skilled in the art will understand it is illustrative in nature.

Other features, aspects, and advantages of the subject matter disclosed herein are provided in the Detailed Description, which follows.

BRIEF DESCRIPTION OF THE DRAWINGS

Drawings are provided herein, which are intended to be illustrative in nature. The drawings are provided to improve clarity of the present disclosure and they are not intended to limit the scope of the invention. Provided schematic diagrams are not drawn to scale.

DETAILED DESCRIPTION

Figure 1:
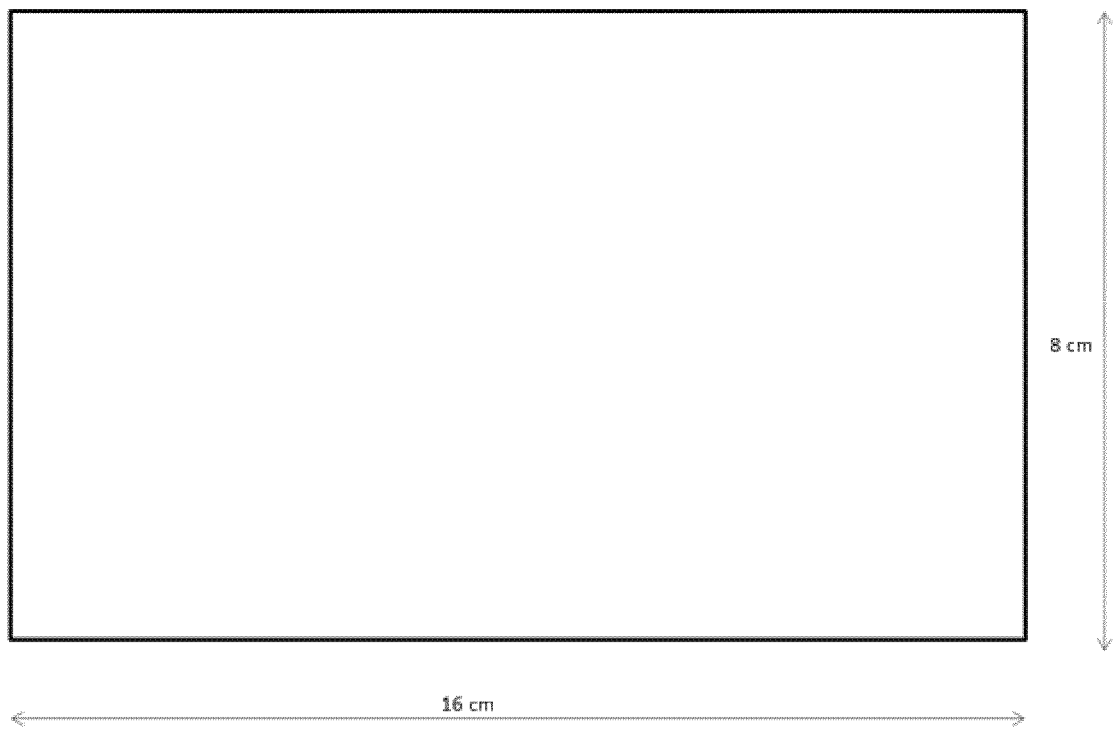
FIG. 1 provides a schematic diagram of an acellular dermal matrix (ADM) having a size and shape commonly used for breast reconstruction.

In the following detailed description, reference is made to the accompanying drawings, which form part of the present disclosure. The embodiments described in the drawings and description are intended to be exemplary and not limiting. As used herein, the term "exemplary" means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Definitions

Unless otherwise defined, each technical or scientific term used herein has the same meaning as commonly understood by one of ordinary skill in the art to which this disclosure belongs. As used herein, certain terms may have the following defined meanings.

As used in the specification and claims, the singular form "a," "an" and "the" include plural references unless the context clearly dictates otherwise.

As used herein, the term "comprising" is intended to mean that the apparatuses, systems, and methods include the recited elements, but do not exclude others. "Consisting essentially of" shall mean that the apparatuses, systems, and methods include the recited elements and exclude other elements of any essential significance to the combination when used for the intended purpose. Thus, an apparatus, system, or method consisting essentially of the elements as defined herein would not exclude other materials, features, or steps that do not materially affect the basic and novel characteristic(s) of the claimed invention. "Consisting of" shall mean that the apparatuses, systems, and methods include the recited elements and exclude anything more than a trivial or inconsequential element or step. Embodiments defined by each of these transition terms are within the scope of this invention.

As used herein, the terms "tissue graft" or "graft" shall refer to any suitable skin or soft tissue implant or mesh, such as, for example, an ADM, a synthetic dermal regeneration system (e.g., Integra® developed by Integra LifeSciences Corporation) or other synthetic graft, an autograft, an allograft, or a xenograft. That is, the graft may be formed of any suitable materials, such as dermal or cellular material from: the patient, one or more different members of the same species, one or more members of different species, or engineered tissue lines. Additionally or alternatively, the graft material may include synthetic or non-animal derived materials, such as, for example, silk (e.g., Seri® silk mesh by Allergan®), polyglactin 910 (e.g., Vicryl® by Ethicon, Inc.®), polydioxanone (e.g., PDS® II by Ethicon, Inc.®), or other suitable synthetic or naturally-derived material.

As used herein, the term "ADM" is an acronym for "acellular dermal matrix", which may be used interchangeably with the term, "acellular tissue matrix (ATM)". As used herein, ADM and ATM each refers to a soft tissue replacement graft formed of an acellular scaffold, such graft may be an allograft or xenograft type material, synthetic, or engineered material.

As used herein, the term "perforations" shall mean small holes or piercings, such as holes formed, for example, by piercing or punching a material, such as a graft. In some embodiments, the perforations are round or substantially round.

As used herein, the term "fenestrations" shall mean elongated slits or incisions. In various embodiments provided herein, fenestrations are provided within a graft and arranged in a plurality of rows with partial overlap of fenestrations in adjacent rows.

As used herein, "overlap" between rows refers to lengthwise (i.e., horizontal) overlap. Said differently, overlap of fenestrations in parallel rows refers to the portion of the fenestrations sharing the same x-coordinates. For purposes of this definition, the orientation of the axes corresponds to the orientation of the fenestrations such that rows of fenestrations are said to be positioned along or parallel to the x-(horizontal) axis, regardless of their orientation relative to the perimeter of the graft.

As used herein, "patient" shall refer to any surgical subject receiving a graft for medical treatment or research purposes. As used herein, a patient may be a human or any other animal. In preferred embodiments, the patient is mammalian.

As used herein, "substantially" shall mean with a margin of error up to 25%. For example, a row of fenestrations that is substantially parallel to an edge of a graft may have individual fenestrations or rows of fenestrations that deviate 0-25% from the parallel axis.

All numerical designations, including ranges, are approximations which are varied (+) or (−) by increments of 0.1. It is to be understood, although not always explicitly stated that all numerical designations are preceded by the term "about".

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. As will also be understood by one skilled in the art, all language such as "up to," "at least," "greater than," "less than," and the like, include the number recited and refer to ranges which can be subsequently broken down into subranges as discussed above.

Improved Grafts and Methods of Making and Using the Same

One embodiment of the present disclosure is directed to an improved tissue graft, such as an ADM. Currently available ADMs are often rectangular in shape. A commonly sized and shaped ADM is shown in FIG. 1; however, the graft of the present disclosure may be of any suitable size or shape. As one non-limiting example, the graft may have the contoured shape shown in FIG. 7.

Figure 2:
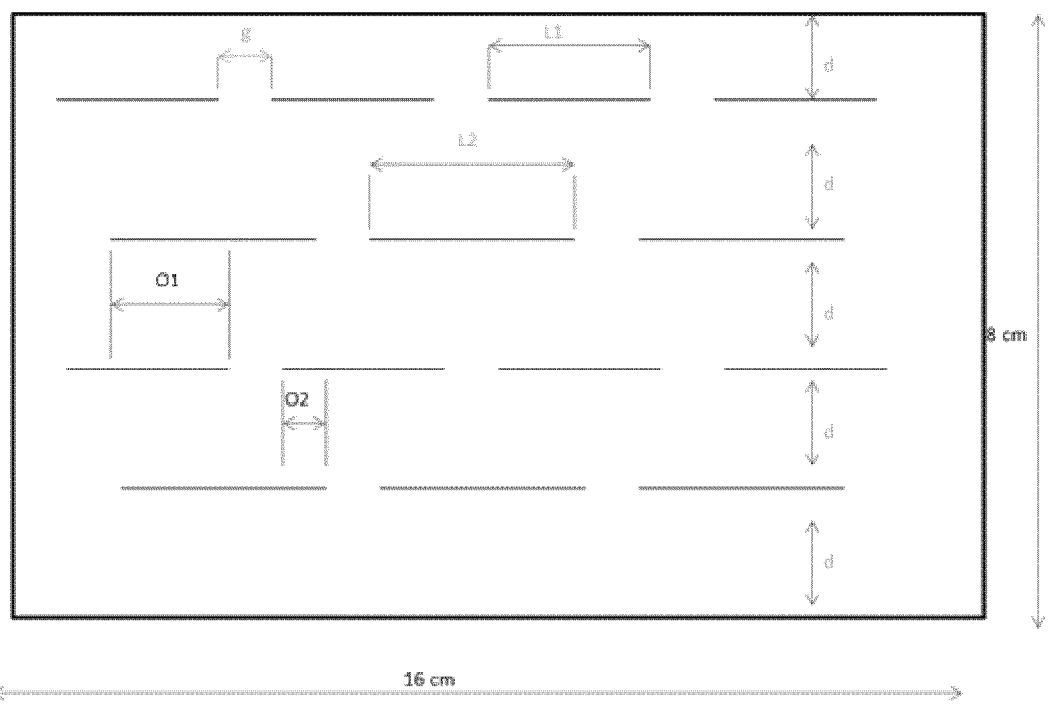
FIGS. 2-7 each provides a schematic diagram of an embodiment of a tissue graft having fenestrations formed in accordance with the principles of the present disclosure.
Figure 3:
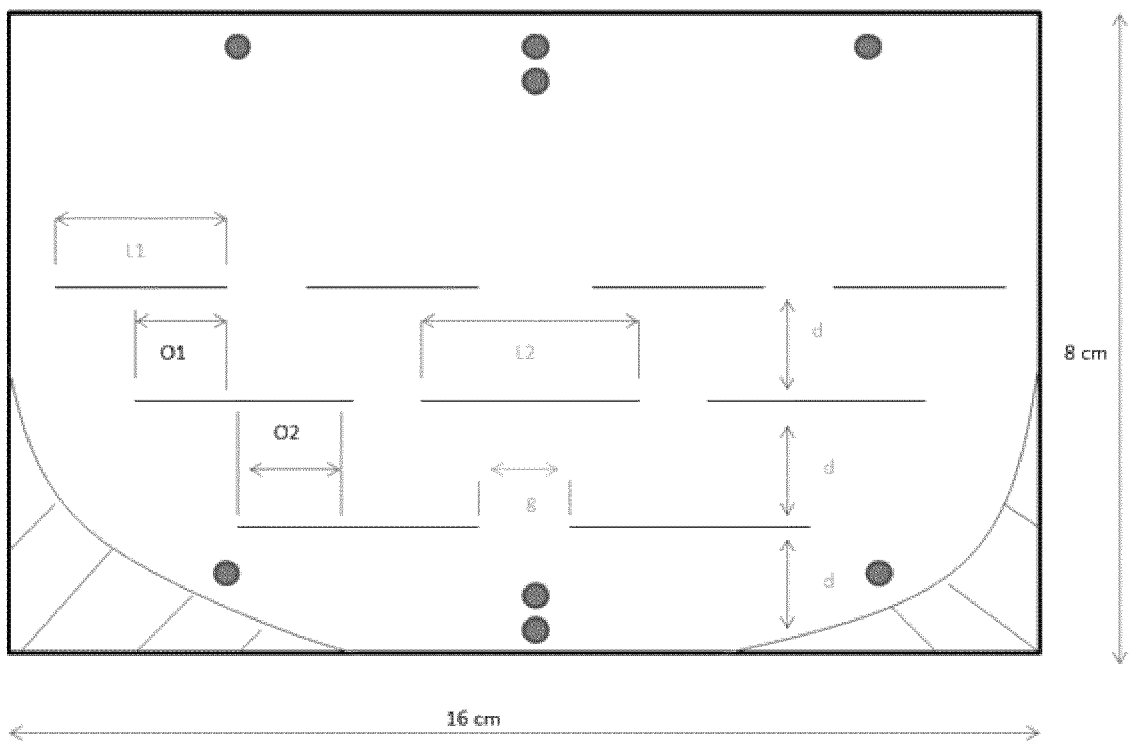
Figure 4:
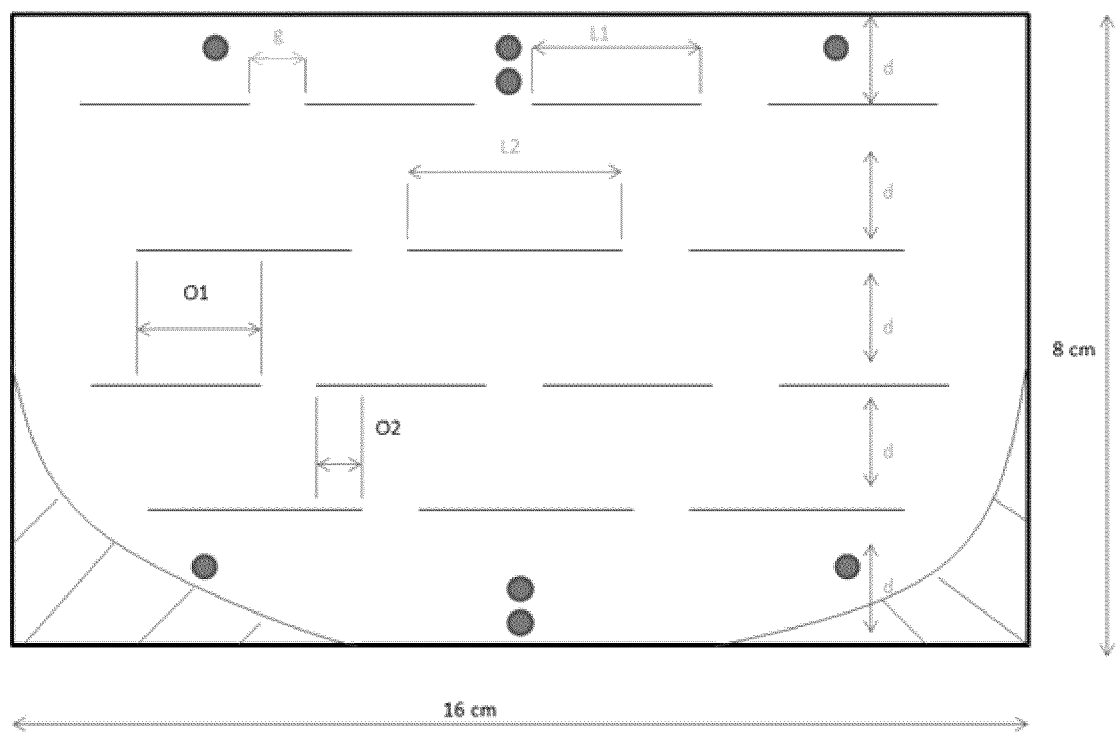

In various embodiments, the graft is improved through the addition of a plurality of fenestrations. In various embodiments, these fenestrations are added to the graft during the manufacturing process. As shown in FIGS. 2 and 4, in some embodiments, the fenestrations are symmetrically placed along the entire surface area of an ADM or other graft. In other embodiments, the fenestrations are asymmetrically placed on an ADM or other graft. For example, as shown in the embodiment of FIG. 3, the fenestrations are concentrated on approximately one half of the graft. In some such embodiments, the fenestrations are concentrated on the caudal half.

Before clinical use of the graft, for example, during the manufacturing process, the ADM or other graft may be further cut, with a plurality of corners discarded, in order to improve the fit of the graft to the desired body part, such as, for example, the breast. An example of such a cut intended for the breast is depicted in FIGS. 3 and 4, where the hashed areas in the caudal corners are cut away and discarded. In some embodiments, alignment perforations may also be added, for example, during the manufacturing process, as shown in FIGS. 3 and 4. In the depicted embodiments, the alignment perforations are circular, but it is contemplated that the perforations may be any suitable shape. Such perforations around the perimeter of the graft may increase operative efficiency and aesthetic outcome by improving the accuracy and speed of product placement and/or alignment. In a preferred embodiment, all cuts, perforations, and fenestrations are made to the ADM or other graft during the manufacturing process so that packaged graft arrives in clinics and/or operating rooms with the fenestration pattern and perforations pre-formed; however, in other embodiments, any and all cuts, perforations, and fenestrations described herein may be made to the graft at an operating room prior to utilization.

Figure 5:
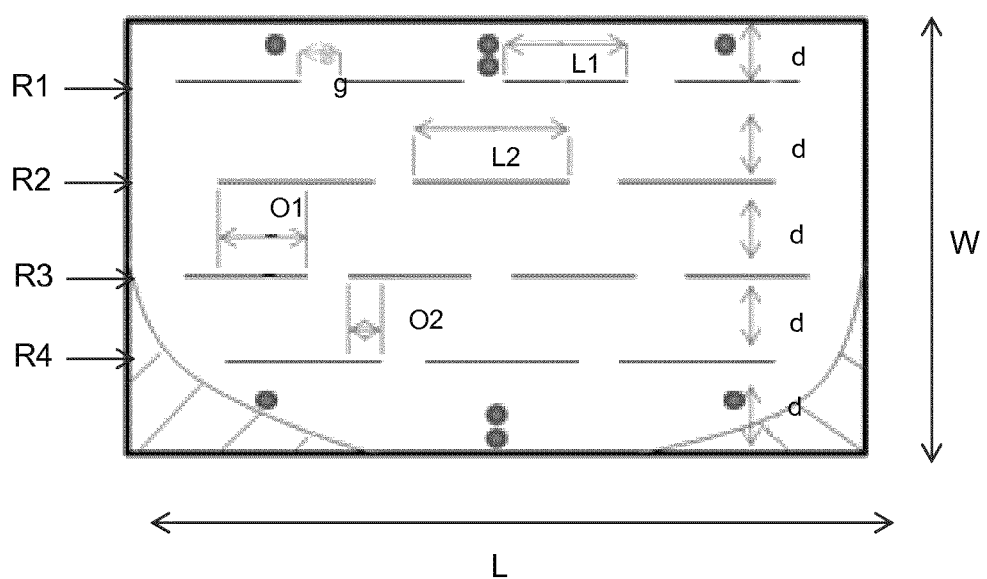
Figure 6:
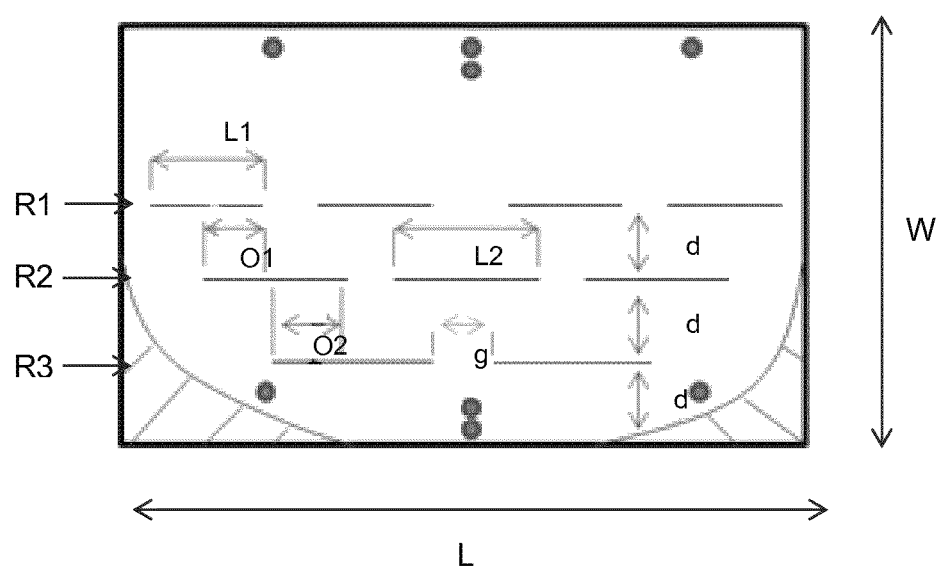

While a variety of fenestration shapes, lengths, and patterns may be used, in a preferred embodiment, the dimensions or ranges of dimensions provided in FIGS. 5, 6, and/or 7 are used.

As shown in FIG. 5, in some embodiments, the fenestrations are aligned in rows and each row is evenly spaced along the width of the graft (where the width of the graft is depicted as the shorter, vertical edge). For example, in the embodiment of FIG. 5, where the width (W) of the graft is 8 cm, the distance (d) between each of the four rows of fenestrations is approximately 1.6 cm, the distance between the top edge and the first row R1 is approximately 1.6 cm, and the distance between the bottom edge and the last row R4 is approximately 1.6 cm.

In one embodiment, the graft is a rectangle having a width (W) of 8 cm and a length (L) of 16 cm; however, in other embodiments, a graft of any suitable size and shape may be used. In some embodiments, to modify the shape of the graft for placement on a breast, the hashed areas in the left and right caudal corners are removed during the manufacturing process or cut and/or removed by the surgical team prior to surgery.

In some embodiments, such as the embodiment shown in FIG. 5, the distance from the ends of the first and third rows (depicted as R1 and R3, respectively) to the nearest side perimeter of the graft is 1-2 cm, and in some such embodiments, about 1.5 cm. In some embodiments, the distance from the ends of the second and fourth rows (depicted as R2 and R4, respectively) to the nearest side perimeter of the graft is 2-3 cm, and in some such embodiments, about 2.5 cm.

In some embodiments, the first row R1 and the third row R3 share substantially the same fenestration pattern, the second row R2 and the fourth row R4 share substantially the same fenestration pattern, and the second row R2 and the fourth row R4 are offset from the first row R1 and third row R3 such that there is partial, but not complete overlap of the fenestrations in adjacent rows. For example, in some embodiments, such as the embodiment depicted in FIG. 5, the overlap between a first fenestration in one row and another fenestration in an adjacent row is 20-90%, and in some embodiments, 50-80% of the length of the first fenestration. Examples of said overlap are shown in FIG. 5 as O1 and O2. To achieve clinically important results, in some embodiments, each fenestration overlaps one or more fenestrations in an adjacent row such that, in total, 20-90%, and preferably, 50-80%, of a given fenestration's length overlaps with fenestration(s) in an adjacent row or rows.

In some embodiments, such as, for example, the embodiment of FIG. 5, each fenestration is at least 2 cm long and each gap (g) between the fenestrations within a row is about 1 cm long. In some embodiments, each gap (g) is 0.5 cm to 1.5 cm in length. In some embodiments, fenestrations in the first row R1 and the third row R3 are 2.1-2.9 cm in length and fenestrations in the second row R2 and the fourth row R4 are 2.5-3.3 cm in length, where the provided ranges are inclusive of the start and end values. In other embodiments, the lengths of the fenestrations may be any individual value or within any subrange therebetween. In one embodiment, the fenestrations in the first row R1 and the third row R3 are 2.5 cm in length; in one embodiment, fenestrations in the second row R2 and the fourth row R4 are 3.0 cm in length. In some embodiments, the fenestrations in all rows are the same or substantially the same length.

Some embodiments of grafts provided herein include perforations to facilitate proper placement and alignment of the graft on a patient. In FIG. 5, these perforations are represented as circles. In some embodiments, each perforation has a diameter or length of 1-3 mm. In some embodiments, at least four perforations are provided; two along the top, cephalic edge and two along the bottom, caudal edge.

As shown in FIG. 5, in some embodiments, eight or more perforations are provided; in FIG. 5, there are four perforations along the cephalic edge and four perforations along the caudal edge. In some embodiments, a perforation is positioned on the top edge at a location 25-50% across the length of the graft, and another perforation is positioned on the top edge at a location 50-75% across the length of the graft. In some embodiments, three or more perforations are placed on the top edge of the graft, each at a separate spaced location 25-75% across the length of the graft. Similarly, in some embodiments, a perforation is positioned on the bottom edge at a location 25-50% across the length of the graft, and another perforation is positioned on the bottom edge at a location 50-75% across the length of the graft. In some embodiments, three or more perforations are placed on the bottom edge of the graft, each at a separate spaced location 25-75% across the length of the graft. In one embodiment, single marking alignment perforations are placed one-third of the way across the top edge, two-thirds of the way across the top edge, one-third of the way across the bottom edge, and two-thirds of the way across the bottom edge. Additionally or alternatively, single or double marking alignment perforations may be approximately centered along (i.e., placed one-half of the way across) the top edge and the bottom edge, for example, to align with the breast meridian.

Another example of a fenestration pattern formed according to the principles of the present disclosure is provided in FIG. 6. The fenestrations of FIG. 6 are positioned within three rows, and the rows are concentrated within a caudal portion of the graft such that a top/cephalic portion comprising one-third to one-half of the graft does not include any fenestrations. As in other embodiments described above, in the embodiment depicted in FIG. 6, there is partial, but not complete overlap between fenestrations of adjacent rows. For example, in the provided embodiment, the overlap O1 between a fenestration in the first row R1 and an adjacent fenestration in the second row R2 is 20-90%, and preferably, 50-80%. Similarly, the overlap O2 between a fenestration in the second row R2 and an adjacent fenestration in the third row R3 is 20-90%, and preferably, 50-80%. In various embodiments, each fenestration overlaps one or more fenestrations in an adjacent row along 20-90%, and preferably, 50-80%, of the length of the fenestration.

The lengths of the fenestrations may vary within a row or between rows, or the length of each fenestration within a graft may be substantially the same. As one non-limiting example of suitable dimensions, in the embodiment depicted in FIG. 6, the graft has a length (L) of 16 cm and a width (W) of 8 cm; each fenestration in the first row R1 has a length L1 within the range of 1.8-2.3 cm and each fenestration in the second row R2 and third row R3 has a length L2 within the range of 3-4 cm. The distance (d) between each row and between the third row R3 and the bottom border is 1.4-1.7 cm. The gap (g) between each fenestration within the first row R1 is 0.8-1.2 cm; the gap (g) between each fenestration within the second row R2 is 0.8-1.2 cm; and the gap (g) between each fenestration within the third row R3 is 1.3-1.8 cm. In one embodiment, the fenestrations in the first row R1 have a length L1 of 2.0 cm and the gap (g) between each first row fenestration is 1 cm, the fenestrations in the second row R2 have a length L2 of 3.5 cm and the gap (g) between each second row fenestration is 1 cm, and the fenestrations in the third row R3 have a length L2 of 3.5 cm and the gap (g) between each third row fenestration is 1.5 cm.

In the embodiment illustrated in FIG. 6, alignment perforations are provided within the graft in an upper right corner, an upper left corner, a lower right corner, and a lower left corner; alignment perforations may also be provided near the center of the upper border and near the center of the lower border. In some embodiments, such alignment perforations are each at spaced locations 25-75% across the length of the graft. In one embodiment, single marking alignment perforations are placed 25-50% of the way across the top edge, 50-75% of the way across the top edge, 25-50% of the way across the bottom edge, and 50-75% of the way across the bottom edge. In one embodiment, single marking alignment perforations are placed one-third of the way across and two-thirds of the way across the top edge and one-third of the way across and two-thirds of the way across the bottom edge. Additionally or alternatively, single or double marking alignment perforations may be centered along (i.e., placed one-half of the way across) the top edge and the bottom edge, for example, to align with the breast meridian.

Figure 7:
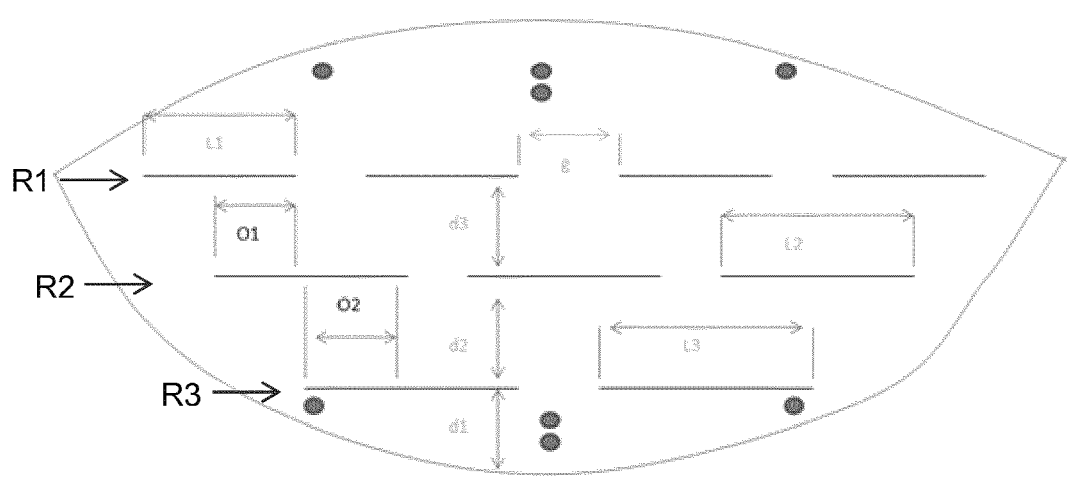

Another embodiment of an improved graft having fenestrations formed therein is provided in FIG. 7. In the graft of FIG. 7, the fenestration pattern is similar to the fenestration pattern in FIG. 6; however, instead of being configured for a rectangular graft, the pattern is configured for an irregularly-shaped, contoured graft designed to match the contours of a human breast. In one example, the graft has a length at its longest horizontal of 14.7 cm and a width at its widest of 7.3 cm. In the illustrated embodiment, the rows of fenestrations are parallel to a horizontal axis; in other contoured embodiments, the rows of fenestrations may be parallel to a curvilinear caudal or cephalic border.

When using a contoured ADM or other contoured graft, any fenestration pattern may be used that achieves desired expansion characteristics. In some embodiments provided herein, such a fenestration pattern has each fenestration overlapping with one or more fenestrations in an adjacent row along 50-80% of the fenestration's length. In various embodiments, the grafts include 3-4 rows of fenestrations with each fenestration being 2-4 cm in length. In some embodiments, fenestrations within a row may be spaced, horizontally, 0.5-2.0 cm apart, and fenestrations in adjacent rows may be spaced, vertically, 1.0-2.0 cm apart.

In the non-limiting example provided in FIG. 7, the fenestrations are offset from the perimeter of the graft. In one embodiment, the distance from the left edge of the graft to the first fenestration in the first row R1 is about 1.5 cm, and the distance from the right edge of the graft to the last fenestration in the first row R1 is also about 1.5 cm. Similarly, the distance from the two ends of the second row R2 to the respective closest side of the graft is about 1.5 cm. The distance from the two ends of the third row R3 to the respective closest side of the graft is about 2 cm. In some embodiments, the distance between each row of fenestrations is approximately 1.4-1.7 cm; in one embodiment, the distance is 1.5 cm. In some embodiments, the distance between the third row R3 of the fenestrations and the bottom edge of the graft is approximately 1.4-1.7 cm; in one embodiment, the distance is 1.5 cm.

In the embodiment of FIG. 7, the first row R1 includes fenestrations each having a length L1 of 1.8-2.4 cm and includes gaps (g) between the fenestrations having a length of 0.8-1.2 cm. In one embodiment, L1 is 2.25 cm and the gap (g) in the first row R1 is 1 cm. In the depicted embodiment, the second row R2 includes fenestrations each having a length L2 of 1.8-2.4 cm and includes gaps (g) between the fenestrations having a length of 0.8-1.2 cm. In one embodiment, L2 is 2.25 cm and the gap (g) in the second row R2 is 1 cm. The third row R3 includes fenestrations each having a length L3 of 2.7-3.2 cm and includes gaps (g) between the fenestrations having a length of 1.0-1.8 cm. In one embodiment, L3 is 3.0 cm. In some embodiments, the overlap lengths O1 and O2 are equal to 50-80% of the length of a fenestration. The perforations of FIG. 7 are sized and positioned the same as, or similarly to, the perforations of FIG. 5.

In one embodiment, fenestrations at least 2 cm in length are used. In some embodiments, at least some of the fenestrations are 3 to 4 cm in length. In some embodiments, at least some of the fenestrations are longer. In one embodiment, at least one row of fenestrations has fenestrations that are 3.5 cm long. In some embodiments, the fenestration patterns provided in any of FIGS. 2-7 may include fenestrations of such dimensions. Such large, strategically designed fenestrations may lead to increased vascularization and incorporation of the graft. Moreover, such large, strategically designed fenestrations may concurrently lead to optimal expansion of the graft as the size and shape of the fenestrations causes them to open up widely, especially in the central aspect.

Another aspect of the disclosure is directed towards improved utilization of an ADM or other graft as an inferior-lateral sling in breast reconstructive surgery. One embodiment of the method includes using an ADM as an inferior-lateral sling to support and optimize tissue expander placement. With respect to the present technology, the hydrated or rehydrated ADM of various embodiments is widely fenestrated in a specific pattern. In one embodiment, the material is fenestrated in three rows, and in another embodiment, four rows. In other embodiments, any of the fenestration patterns disclosed herein may be used. In some embodiments, the method further includes placing a tissue expander in a partial submuscular or subcutaneous plane with the inferior-lateral portion of the expander pocket constructed using the fenestrated ADM. In some embodiments, the method further includes suturing the superior edge of the ADM to the inferior portion of the pectoralis major muscle. The medial, lateral, and inferior edges may also be sutured in an interrupted fashion to the inframammary fold (IMF), which additionally helps in defining the medial, inferior, and lateral breast borders. The method of some embodiments additionally includes placing the expander in the partial submuscular or subcutaneous and ADM pocket and filling it to an appropriate volume using a closed system with sterile saline. A drain may be placed in the subcutaneous plane and the skin incision closed.

Modeling the effects of fenestrations on the properties of the ADM or other graft requires acknowledgement of the graft as a material with a uniform Young's modulus. For breast reconstruction, the aggregate effect of symmetrically arranged fenestrations on the graft's mechanical properties is explained by a uniform reduction in the effective Young's modulus in a direction perpendicular to the chest wall in the area of graft fenestration. Asymmetric reduction of the Young's modulus is achieved by concentration of the fenestrations at either the cephalic or caudal ends of the graft.

The relaxed Young's modulus facilitates an increased deflection of the graft from its resting, unaltered state under the weight of the breast implant or tissue expander and is modeled using the following equation:

$$\begin{cases} -\partial_y(\sigma \partial_y u) = f, & y \in (0, l), \\ u(0) = 0, \\ u(l) = 0, \end{cases}$$

Figure 8:
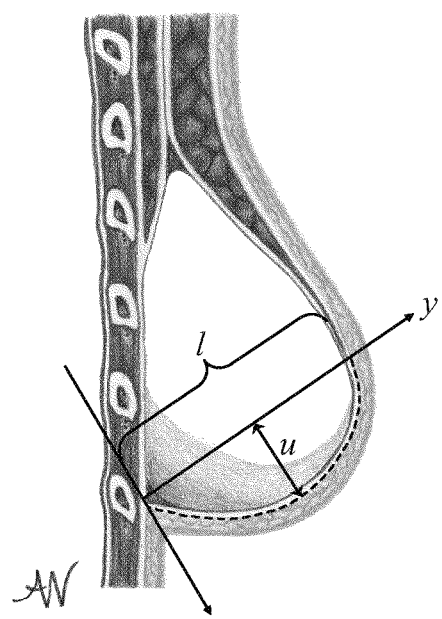
FIG. 8 depicts a cross-sectional schematic view of a human breast having an implant disposed therein.

This equation represents a one-dimensional boundary value problem used to describe the geometry of the graft where σ represents the Young's Modulus of the material, u denotes the amount of deviation of the graft from its flat, unstressed state, f is the load stemming from the implant, y is distance from the chest wall in a posteroanterior direction, ∂y is the derivative of u in the direction of y, and l is the width of the graft or the distance from the suture point at the chest wall to the point of attachment at the pectoralis major muscle. FIG. 8 depicts the physical parameters of the graft used to predict the deflection (u) from a flat, unstressed state.

The reduced inferior pole tension allows for enhanced expansion under the weight of the breast implant or tissue expander. The effects of asymmetrically arranged fenestrations are similarly modeled and appear to afford the surgeon greater precision in controlling inferior pole characteristics.

In order to create a mathematical model to describe the expansion of the graft under the weight of an implant, the 3-dimensional contour of the inferolateral aspect of the reconstructed breast was simplified into a 1-dimensional problem in order to simulate the deflection of the graft from its resting state. In other words, the final shape of the graft, which is affected by manipulation of the variables in the equation above (e.g., the graft's inherent Young's modulus, the graft's position on the chest wall, and the weight of the implant), is described simply as the amount of bend, or deflection, of the graft from its flat, unstressed state. This variable is denoted as u.

The ultimate result of the fenestrations is dependent upon augmentation of an intrinsic property of the graft known as Young's modulus (σ). Young's modulus is defined as the inherent stiffness of an elastic material, and is mathematically represented by the ratio of stress (pounds per square inch) over strain (dimensionless). Given that the commonly-used rectangular ADMs have a set size and fixed, uniform elastic properties, they have a particular Young's modulus that determines their behavior under stress. A greater Young's modulus predicts that under a given stress, the ADM (or other graft) will demonstrate less deviation (u) compared to a material with a lower σ. By placing fenestrations in the graft, the effective Young's modulus is reduced to a lower σ, and yields a larger deflection profile (u), consequently improving expansion of the inferior pole and facilitating a more natural shape under the load of the implant.

Figure 9:
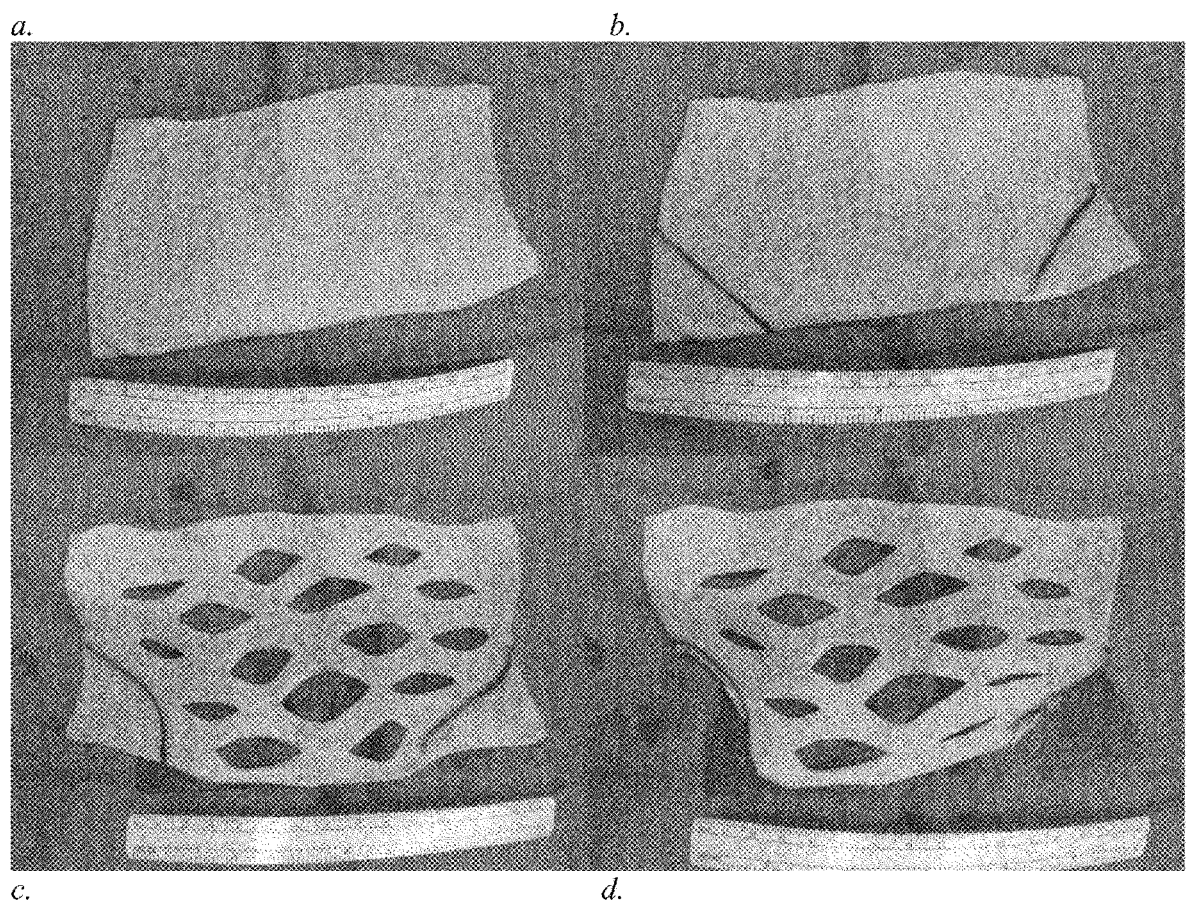
FIG. 9 provides photographic images of an ADM in various stages of preparation. The series of photographs together depict a method of preparing ADM in accordance with the principles of the present disclosure.
Figure 10:
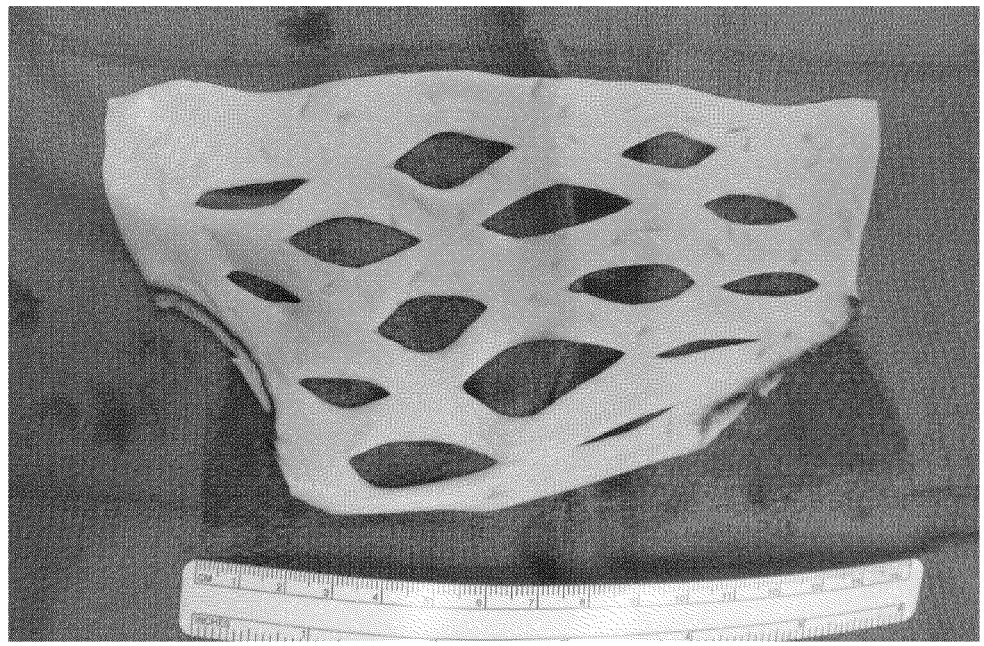
FIG. 10 provides a photographic image and a schematic diagram of one embodiment of an ADM having fenestrations formed in accordance with the principles of the present disclosure.
Figure 10:
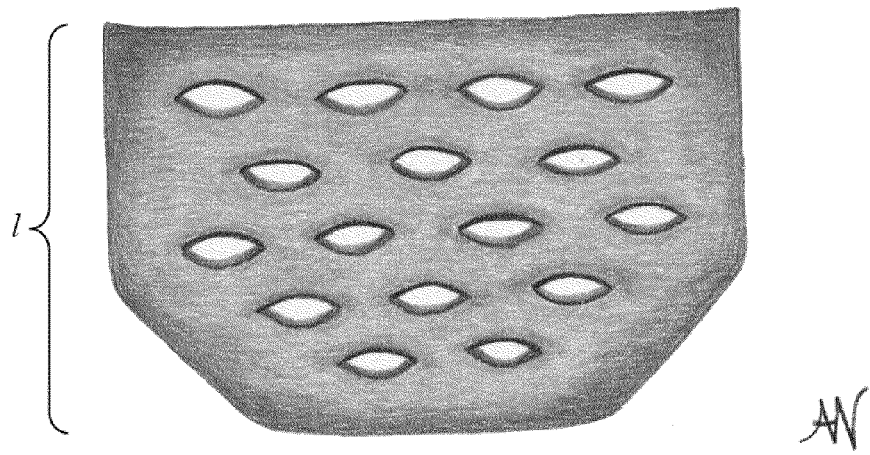

For breast reconstructions, reducing the Young's modulus requires that fenestrations be placed perpendicular to a posteroanterior line extending directly off the chest wall, as depicted in FIG. 8 by the vector y, which signifies distance from the chest wall toward the suture point at the inferior edge of the pectoralis major muscle. Specifically, fenestrations of a predetermined length are made in the direction of the longest aspect of the rectangular or shaped graft or parallel to the ADM (graft) border. Upon inset of the graft, these precise fenestrations (achieving approximately 20-90%, or in some embodiments, 50-80%, overlap) open wide, assuming and maintaining an oval or substantially oval shape. If the fenestrations are regularly spaced within parallel rows and the rows are staggered as depicted in FIGS. 9 and 10, an approximately uniform effective Young's modulus can be achieved and calculated by integrating over the distance from the chest wall to the anterior fixation point of the graft at the pectoralis major muscle (y).

The deflection of the graft under the weight of an implant can be described using the one-dimensional boundary value problem provided above. As previously mentioned, u denotes the deviation of the graft from its flat, unstressed state. This deflection profile is essentially affected by changes in two variables: y and σ. The variable y must have a value that is bound between 0, which represents the suture point on the chest wall at the level of the IMF and l, which is the distance from this point to the attachment at the pectoralis major muscle, or the width of the graft in the unstressed position (FIG. 8). The second variable is the effective Young's Modulus, σ, that is relaxed by placing fenestrations in the graft. The equation for the one-dimensional boundary value problem also includes an additional variable, f, which is the load stemming from the implant and is assumed to be constant. Clinically, the pectoralis major muscle is dynamic in nature in that the inferior edge "window shades" following implant or expander placement. This phenomenon, however, does not impact the conclusions as the boundaries of the equation include the suture point at the pectoralis, which negligibly adjusts in direct proportion to muscle displacement.

It is realistic to assume that this linear elasticity model is valid in practice due to relatively small deflections from equilibrium. Even if the parameters σ, l, and f are unknown, and σ is the only variable that is manipulated, the presence of fenestrations in the ADM will always lead to an enhancement in inferior pole expansion. This is depicted graphically in FIG. 11 where graft deflection profiles for arbitrary values for a are plotted, demonstrating that a decreasing Young's modulus will increase the deviation of the graft from its resting, unstressed state. Accordingly, fenestrating the graft, which decreases σ, is shown to result in enhanced graft deflection.

The above-provided equation for the one-dimensional boundary value problem models the situation in which cuts are placed uniformly perpendicular to l, which results in a symmetric deflection between the two suture points at y=0 and y=1. It is conceivable to instead generate an asymmetric deflection profile by concentrating the cuts at the cephalic or caudal portion of the graft with respect to the chest wall. The resultant shape can be predicted using the following profile function:

$$\sigma(y) = a + (1-a)[1 + \tan h(10(x-0.5))]/2$$

in which "a" represents the targeted effective Young's modulus (σ) for an asymmetric deviation. The new Young's modulus is now inhomogeneous across the graft.

Figure 12:
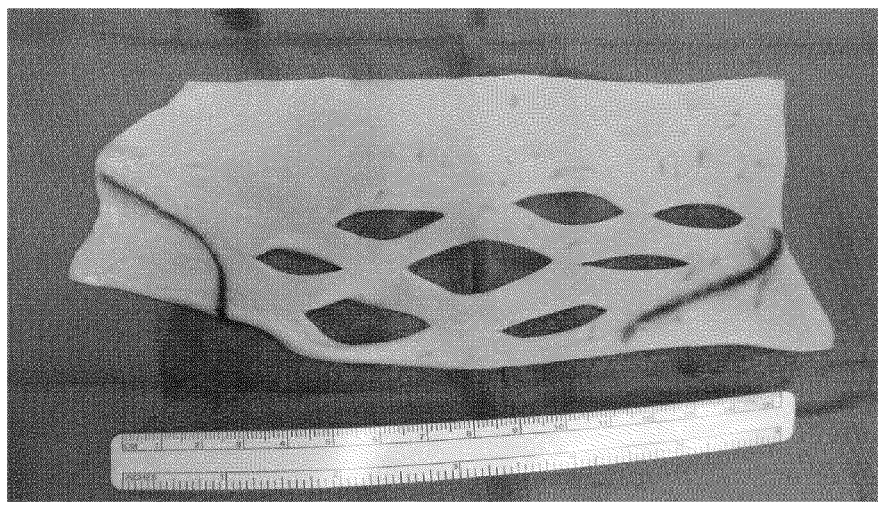
FIG. 12 provides a photographic image and a schematic diagram of another embodiment of an ADM having fenestrations formed in accordance with the principles of the present disclosure.
Figure 12:
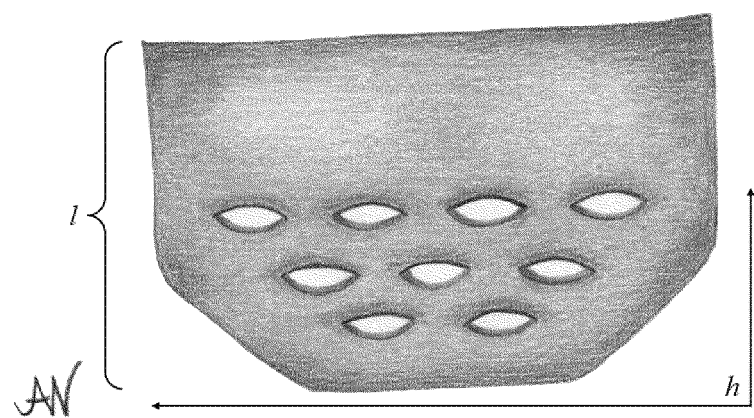
Figure 13:
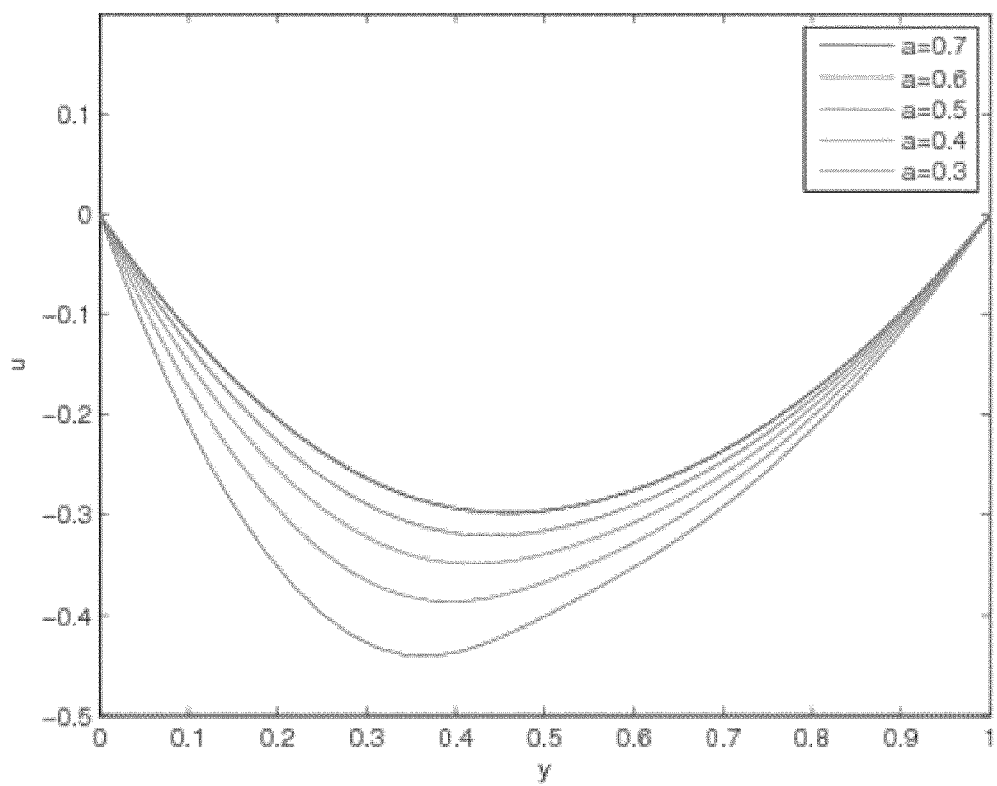
FIG. 13 provides a graph depicting various profiles of Young's Modulus ($\sigma$) across the length of an ADM following the inhomogeneous placement of fenestrations.

For example, if, as in FIG. 12, the fenestration cuts are not spread out over the entire width l, but are instead symmetrically concentrated within the area h, which denotes the caudal half of l, the effective Young's modulus will no longer be constant over l. FIG. 13 demonstrates the effect of concentrating the fenestrations closer to the chest wall (caudal end of the graft), specifically showing a profile of the local effective Young's Modulus (σ) across the length of the graft following the inhomogeneous placement of fenestrations. As shown, concentrating the fenestrations closer to the chest wall results in a reduced Young's modulus in this portion of the graft compared to the unfenestrated portions of the graft. This reduced Young's modulus in turn precipitates an asymmetric deflection profile of the graft with respect to chest wall proximity as seen in FIGS. 13 and 14.

Figure 11:
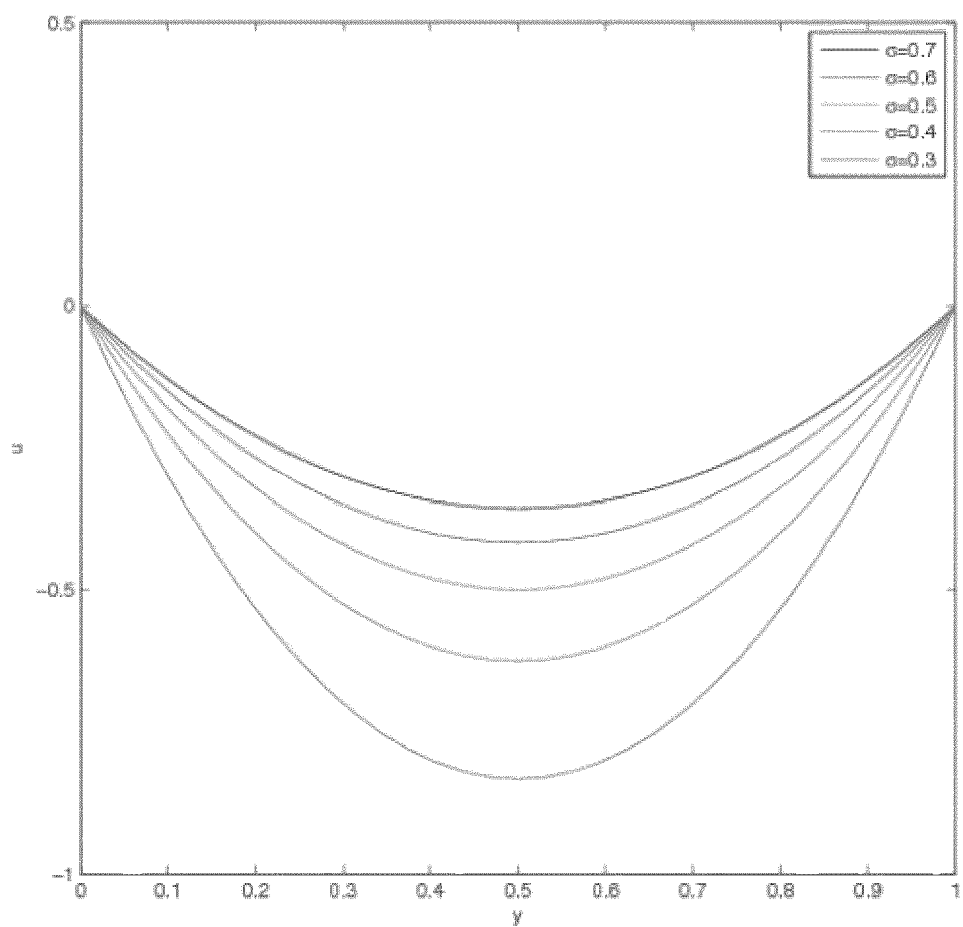
FIG. 11 provides a graph depicting graft deflection profiles for values of $\sigma$.
Figure 14:
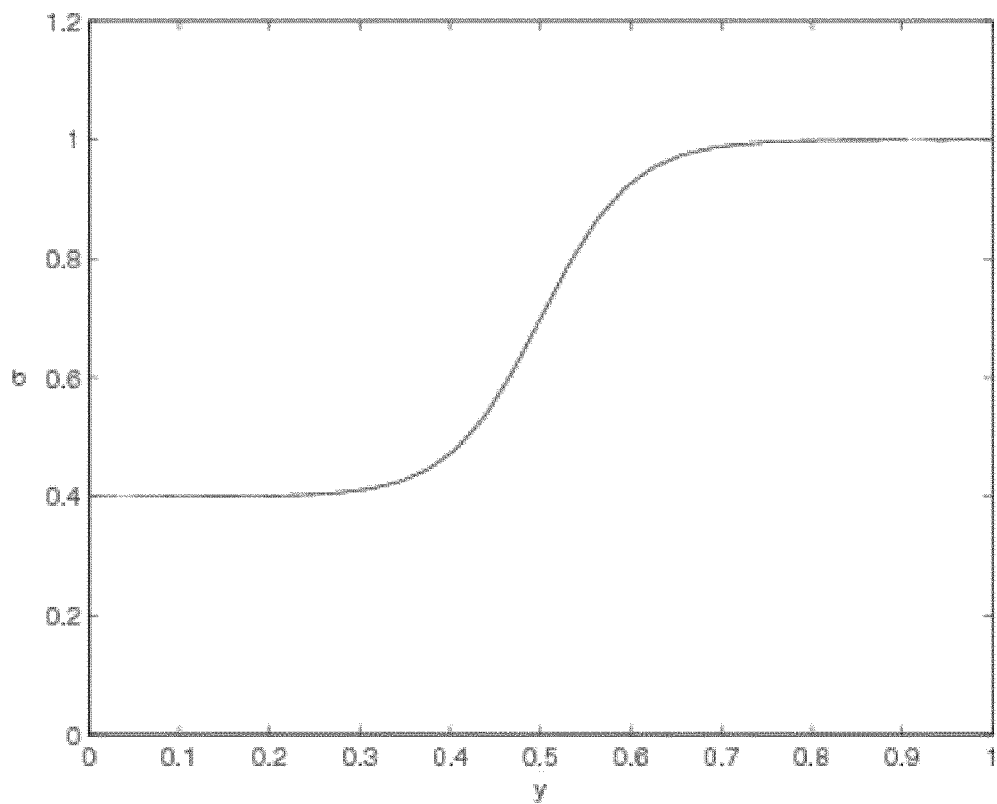
FIG. 14 provides a graph depicting a graft deflection profile for an inhomogeneous Young's modulus.

In particular, FIG. 14 depicts a graft deflection profile for an inhomogeneous Young's modulus as modeled by the asymmetric deflection profile equation provided above. Asymmetric concentration of the fenestrations from y=0 to y=0.5 confines the deflection of the graft to a position closer to the chest wall. This is in contrast to the deflection profile for a homogeneous fenestration pattern, which is depicted in FIG. 11.

Studies report that ADMs enhance the aesthetics of the reconstructed breast by defining the infra- and lateral-mammary folds[15, 16], as well as by facilitating a more desirable expansion of the inferior pole of the breast[18, 19]. Topol et al. attribute improved projection at the inferior pole to an easing of the tension placed on the implant as a result of the ADM incorporation[12]. This expansion is accentuated by altering the elastic properties of the ADM through strategically placed fenestrations with appropriate overlap. As the cuts in the ADM decrease the effective Young's modulus and consequently increase the deflection of the ADM under a fixed load, the tension on the implant similarly decreases, which is responsible for expansion of the inferior breast pole to a greater degree than that which has previously been described in the literature.

In some embodiments of the techniques described herein, a pattern of precisely staggered and overlapping cuts arranged into parallel rows spread uniformly over the surface of the grafted material is used. In certain embodiments, the graft material is an ADM. By organizing the cuts parallel to the long axis of the ADM in the medial to lateral direction, the effective Young's modulus is reduced in breast reconstructions along a vector connecting the fixation point at the chest wall to the inferior border of the pectoralis major muscle in the posteroanterior direction (y). Given that maximum expansion of a graft occurs when it is pulled perpendicular to the length of the cuts, the fenestrated ADM will undergo maximum expansion under the weight of the implant or tissue expander using this technique. Decreasing the vertical distance between rows of cuts exponentially decreases the amount of graft expansion, and decreasing the absolute length of the cuts linearly decreases graft expansion. Additionally, given that maximal excursion occurs at the center of the fenestration, according to the expanded-metal principle, optimal uniform expansion is achieved when the cuts are offset or staggered in alternate rows to achieve 50-80% overlap. This also results in the shortest healing time, as the islands of uncut tissue are free to act as bridges to facilitate tissue ingrowth. This also leads to more tissue to tissue contact (abutment) which should allow greater and more rapid vascular ingrowth and decreased infection rates. Just as concentrating the cuts on the distal, or caudal, portion of the ADM near the chest wall precipitates asymmetric deflection of the ADM, manipulating these variables may allow for control of the extent of ADM deviation under the implant and therefore influence the degree and direction of lower pole expansion.

As noted above, complications associated with non-fenestrated ADMs are generally reported to be comparable to reconstructions that do not utilize ADM[10, 27]. However, several studies have also shown increased rates of seroma formation in patients who have undergone Alloderm-associated (LifeCell Corp., Branchburg, N.J.) reconstructions[25, 26, 30, 31] with an incidence ranging from 0 to 9 percent in one particular systematic review[10]. Irregularity at the soft-tissue interface, resulting in poor contact between the ADM and overlying tissue[21] and intentional under inflation of the tissue expander[17] have been cited as reasons for increased seroma rates in patients undergoing reconstructions with non-fenestrated ADMs.

Precise fenestrations, as provided in various embodiments herein, with optimal overlap, minimize the risk factors associated with increased seroma rates and improve incorporation rates. In a patient population, a decreased rate of seroma formation was subjectively observed in patients who underwent reconstruction with fenestrated ADMs. The cuts in the ADM and consequently enhanced deflection of the ADM may allow for a tighter approximation of the tissue expander and ADM to the overlying soft tissue. In addition, the fenestrations create a communication between the subpectoral pocket and the subcutaneous pocket, allowing drainage of fluid into the more superficial pocket that can be drained with a single drain. Earlier tissue expansion and pressure on the ADM leads to material thinning, earlier vascularization, and greater tissue incorporation due to increased approximation of the graft to the breast flap. This decreases the potential for infectious complications, as there is earlier vascular in-growth into the ADM.

In other embodiments, the techniques, features, and advantages discussed above are applicable to applications other than breast reconstruction. Graft materials having strategically placed fenestrations may provide advantages over non-fenestrated grafts when used in any location of the body having a curvature and/or when used for an application in which expansion of the graft is desired. In some embodiments, fenestrated grafts, such as, for example, grafts having any one of the fenestration patterns described above, are used in abdominal hernia repairs, buttocks augmentation procedures, chest wall reconstructions, and scalp reconstructions. The fenestrated grafts may be used, for example, for improved skin and/or soft tissue grafts, used, for example, with grafting treatments following severe trauma, surgery, burns, infections, or cancer to the skin, or for any other suitable purpose.

In various embodiments, all fenestrations within a graft are aligned along the same axis or an axis parallel to other fenestrations. In some embodiments, some or all fenestrations are oriented such that the elongated axis of each fenestration lies substantially or completely horizontally. In some embodiments, some or all fenestrations are positioned with the elongated axis of the fenestrations parallel or substantially parallel to one or more perimeters (i.e., edges or borders) of the graft material. In some such embodiments, each row of fenestrations is parallel or substantially parallel to a cephalic and/or caudal border of the graft material. The grafts of some embodiments may have one or more curved edges, such as a curved cephalic and/or caudal border; in such embodiments, the rows of fenestrations may lie parallel to the curved border and share the same or substantially the same curvilinear shape. In some embodiments, the rows of fenestrations are oriented in a direction perpendicular or substantially perpendicular to the axis of major expected stress on the graft. Such an orientation allows for faster and enhanced expansion. In some embodiments, the rows of fenestrations are oriented in a direction perpendicular or substantially perpendicular to the axis along which maximal curvature is desired. Herein, substantially perpendicular may mean within ±5 degrees, ±10 degrees, ±15 degrees, ±20 degrees, or ±25 degrees of perpendicular.

Advantageously, the fenestrated grafts described herein may achieve intra-graft increased vascular ingrowth, increased and/or faster incorporation of the graft material into surrounding tissue, and decreased seroma rates, compared to non-fenestrated grafts. The fenestrations facilitate the intra-graft vascular ingrowth as well the faster product integration. Infectious complications are reduced with faster incorporation of the ADM due to improved vascular in-growth owing to product thinning due to greater immediate expansion and better abutment of the product to subcutaneous tissue, which contains the blood supply required for proper product integration.

Additionally, the fenestrations allow for increased expansion of the graft material compared to non-fenestrated grafts, allowing surgeons to cover a surgical site of a given size with less graft material.

Moreover, the various fenestration patterns described herein create spaces within grafts. The spaces created within the grafts may serve as effective sites for delivering materials to tissue surrounding and/or underlying the graft. As non-limiting examples, the spaces may serve as effective sites for suturing, drug delivery, stem cell delivery, stromal vascular fraction delivery, or any other suitable delivery. Additionally or alternatively, the spaces may allow for effective incorporation of other materials into the graft. Such materials may include, but are not limited to, mesh, fat tissue, stem cells, and/or an antibiotic eluting material. In some embodiments, such materials are disposed within the spaces formed by the expanded fenestrations.

Example

A retrospective chart review was conducted of the surgical experience and patient outcomes of two surgeons at the Aesthetic and Plastic Surgery Institute at the University of California Irvine over four years utilizing one embodiment of a fenestrated ADM in two stage breast reconstruction.
Research Design and Methods Specifically, an Institutional Review Board-approved retrospective chart review was conducted of two-stage breast reconstructions utilizing ADM at the Aesthetic and Plastic Surgery Institute at the University of California Irvine from 2008 to 2012 (IRB #2012-8663). The billing records and operative reports of two Plastic and Reconstructive surgeons were evaluated to identify patients that underwent two-stage breast reconstruction with tissue expander/implant reconstruction with allograft.

In order to adequately identify all patients, billing codes for breast reconstruction, immediate or delayed, with tissue expander, acellular dermal allograft, trunk, and implantation of a biologic implant for soft tissue reinforcement were searched in the billing database to include all patients that had undergone breast reconstruction surgery utilizing tissue expanders and allograft.
Subjects Participants included all women who underwent mastectomy followed by immediate breast reconstruction utilizing tissue expanders at the University of California Irvine between 2008 and 2012. Exclusion criteria included a history of previous breast surgery including implant placement or delayed reconstruction.

Multiple data points were collected on each patient including type of mastectomy incision, presence or absence of fenestrations, tissue diagnosis, history of smoking, presence of co-morbid conditions including diabetes, pre-operative or post-operative chemotherapy, radiation therapy, and body mass index (BMI) as outlined in Table 1.

Additional operative details were recorded including type of allograft (i.e., ADM) [AlloDerm (LifeCell Corporation, Branchburg, N.J.), AlloMax (Bard, Inc., Warwick, R.I.), or FlexHD (MTF, Edison, N.J. and Ethicon, Summerville, N.J.)], size of allograft, presence of fenestrations, drain placement, tissue expander make, profile, and size, and intra-operative fill volume. Finally, information was collected from the clinic chart regarding subsequent outpatient postoperative expansions with regard to fill volume, time to full expansion, drain removal and dates of subsequent surgery.

Patients were followed for a minimum of one year to allow adequate collection regarding operative outcome and major or minor complications. Major complications were defined as complications requiring invasive treatment, such as implant exchange or seroma aspiration, while minor complications were defined as those treated with expectant management or antibiotics for issues such as cellulitis.
Surgical Technique/Intervention The two surgeons applied one embodiment of the methods disclosed herein, which is an improved method of breast reconstruction utilizing ADM as an inferior-lateral sling. This technique uses the ADM to create an inferior-lateral sling prior to tissue expander placement. In the method that the surgeons applied, the ADM is widely and specifically fenestrated in three to four rows using a scalpel in an unambiguous fashion prior to implantation (FIG. 9). The tissue expander is then placed in a partial submuscular plane with the inferior-lateral portion of the expander pocket created by the fenestrated ADM. The superior edge of the ADM is then sutured to the inferior portion of the pectoralis major muscle (that had been previously released from the chest wall) using interrupted absorbable sutures, which are "parachuted" in order to safely and accurately place the tissue expander. The medial, lateral, and inferior edges are also sutured in an interrupted fashion to the IMF, which additionally helps in defining the breast borders. At the outset, the ADM is marked in the midline in order to correlate this portion of the ADM to the breast meridian. During inset, pleats in the product between the suture points are intentional in order to account for the stretch required during immediate expansion from the unexpanded, resting state. The expander is then filled to an appropriate volume, using a closed system with sterile saline, whereby the skin incision is easily closed without tension and without any undue strain on the pectoralis muscle. A single 15 French round drain is placed in the subcutaneous plane and the skin incision closed.

The ADM was incorporated with patient's mastectomy flaps at the time of implant exchange. Following the completion of tissue expansion, patients underwent implant exchange, often with subsequent nipple reconstruction and tattooing.
Statistical Methods In the observed patient population, the fenestrated and non-fenestrated ADM groups were unequal in size. Tissue expander characteristics and fill dynamics of the fenestrated and non-fenestrated ADM groups were analyzed using the Wilcoxon Rank-Sum test, as the groups were not normally distributed. Table 2 summarizes statistics comparing the fenestrated and non-fenestrated groups.
Results The patient population included 42 patients with two stage reconstruction totaling 70 breasts. In six patients (seven breasts), the ADM was non-fenestrated. In this non-fenestrated population, five reconstructions utilized FlexHD (MTF, Edison, N.J. and Ethicon, Summerville, N.J.), while the other two reconstructions used AlloDerm (LifeCell Corporation, Branchburg, N.J.). Fenestrated ADM, including six FlexHD reconstructions (MTF, Edison, N.J. and Ethicon, Summerville, N.J.), 14 AlloMax reconstructions (Bard, Inc., Warwick, R.I.), and 43 AlloDerm reconstructions (LifeCell Corporation, Branchburg, N.J.), was used in 63 breasts.

There were five major breast complications requiring removal of tissue expanders for infection or extrusion, with two additional tissue expanders requiring explanation for cancer recurrence. There were three minor complications involving wound infection and/or small fluid collection without the need for aspiration or explanation. Additionally, complication rates within 30 and 90 day post-operatively were compared for each of the three types of allograft (Alloderm, FlexHD, and Allomax) used in this patient population. There were 45 breasts reconstructed with fenestrated Alloderm. Two patients required removal of the tissue expander within 30 days (4.4%) and there were no additional tissue expander removals within 90 days (4.4% total). One of the patients had a history of radiation therapy and was receiving chemotherapy at the time of explanation, while the other did not have any identifiable risk factors. There were 12 breasts reconstructed with fenestrated Allomax and one tissue expander was removed within 30 days (8.3%) in a patient who was receiving chemotherapy. There were two additional tissue expanders removed in patients reconstructed with fenestrated Allomax within 90 days (25.0% total). One of these patients had a significant history of tobacco use and the other patient received radiation therapy. There were six breasts reconstructed with fenestrated FlexHD and there were no tissue expander removals within 30 days and one tissue expander removal within 90 days (16.7% total) in a patient who received radiation therapy. The total complication rate requiring tissue expander removal was 6/70 breasts within 90 days or a total complication rate of 8.6%. This data is summarized in Table 3.

Patient group demographics, including age and body mass index (BMI), were determined to be of varying significance. The groups were determined to be alike in age (p=0.3229) but were statistically different for BMI where the BMI for non-fenestrated and fenestrated groups were 21.5 and 26.2 respectively (p=0.0289) (Table 2).

Differences in tissue expander characteristics and fill dynamics between the two groups were also statistically significant including mean expander size, intra-operative fill volume, intra-operative fill percent, number of post-operative expansions, and total fill volume (Table 2). Mean expander size for non-fenestrated and fenestrated groups were 407.1 cc and 546.6 cc, respectively (p=0.0244); intra-operative fill for non-fenestrated and fenestrated groups were 117.1 ml and 291.2 ml, respectively (p=0.0031); percent intra-operative fill for non-fenestrated and fenestrated groups were 28% and 52%, respectively (p=0.0071); percent intra-operative fill compared to total fill for non-fenestrated and fenestrated groups were 27% and 46%, respectively (p=0.0103); number of postoperative expansions for non-fenestrated and fenestrated groups were 4.86 and 3.81, respectively (p=0.0384); and total fill for non-fenestrated and fenestrated groups were 399.3 ml and 570.3 ml, respectively (p=0.0106). Expansion rate between non-fenestrated and fenestrated groups was also statistically significant different (69 ml/fill versus 127 ml/fill, p=0.0033).

There was no statistically significant difference identified between the non-fenestrated and fenestrated groups with regard to office fill per expansion (59.6 ml/fill versus 81.5 ml/fill, p=0.0608); days until drain removal (13.9 versus 14.0 days, p=0.8324); percent of tissue expander volume filled (98 versus 108%, p=0.2706); or the number of days from completion of expansion until implant exchange (116 versus 89.5 days, p=0.1815). Twenty-two patients underwent implant exchange (42 breasts) on average 2.9 months following completion of tissue expansion. The average final implant size was 526 cubic centimeters. There were no significant capsular contractures noted in in this patient group with an average baker grade of 1.14 and mean follow-up period of 7.4 months. Thirty-six percent of the patients undergoing implant exchange received adjuvant chemotherapy and/or radiation therapy. This partially explains the relatively long time period between tissue expander placement and implant exchange as the final reconstruction was delayed until primary cancer-related treatment was completed.

TABLE 1

Patient characteristics

| | Non-Fenestrated (SD) | Fenestrated (SD) |
|---|---|---|
| Total Breasts | 7 | 63 |
| Tobacco smoking history | 1 | 7 |
| Neoadjuvant chemotherapy | 2 | 18 |
| Radiation therapy | 4 | 12 |

TABLE 2

Tissue Expander Statistics

| | Non-Fenestrated Mean (SD) | Fenestrated Mean (SD) | p* |
|---|---|---|---|
| Age, years | 51.33 (14.8) | 46.78 (10.49) | 0.3229 |
| BMI, kg/sq. m | 21.52 (1.33) | 26.17 (5.22) | 0.0289 |
| Expander Size, cc | 407.14 (53.45) | 546.59 (165.92) | 0.0244 |
| Intraoperative Fill, ml | 117.14 (85.97) | 291.21 (167.21) | 0.0031 |
| Total Fill, ml | 399.29 (117.35) | 570.27 (168.58) | 0.0106 |
| # of Postoperative Expansions | 4.86 (0.69) | 3.81 (1.52) | 0.0384 |
| Expansion Rate (ml/fill) | 69.36 (22.25) | 127.10 (58.27) | 0.0033 |
| Office Fill per Expansion, ml | 59.56 (18.08) | 81.53 (80.25) | 0.0608 |
| Intraoperative Fill/Expander Size | 0.28 (0.18) | 0.52 (0.22) | 0.0071 |
| Total Fill/Expander Size | 0.98 (0.26) | 1.08 (0.15) | 0.2706 |
| Intraoperative Fill/Total Fill | 0.27 (0.14) | 0.46 (0.17) | 0.0103 |
| Days with Drain in Place | 13.86 (10.3) | 13.97 (6.52) | 0.8324 |
| Days to Full Expansion | 116 (1292.9) | 89.5 (102.4) | 0.1815 |
| Implant Size, cc | 338.5 (4421.97) | 526.8 (170.62) | 0.0219 |

*Wilcoxon Rank-Sum Test

TABLE 3

Tissue expander removal within 30 and 90 days post-operatively divided by fenestrated acellular dermal matrix type (AlloDerm, FlexHD, Allomax)

| Fenestrated Allograft (ADM) Material | Explantation within 30 days (percentage) | Explantation within 90 days (percentage) |
|---|---|---|
| Alloderm | 2/45 (4.4%) | 2/45 (4.4%) |
| FlexHD | 0/6 (0%) | 1/6 (16.7%) |
| Allomax | 1/12 (7.1%) | 3/12 (25.0%) |
| Total | 3/63 (8.3%) | 6/63 (8.6%) |

Findings

The surgeons altered the existing and popular inferior-lateral sling technique by including strategically placed fenestrations with desired overlap of the fenestrations in adjacent rows. As described previously, following fenestration design (e.g., ensuring appropriate overlap of the fenestrations with respect to each other) and creation, the ADM was inset in the inferior-lateral sling position. It was then sutured in both the pectoralis major muscle and the IMF while taking care to keep the midline of the product aligned with the breast meridian. Muscular and fascial dissection was minimized, which facilitated greater control over tissue expander placement, enhanced inframammary fold definition, decreased pain and a more precise tissue expander pocket creation.

Also of interest, breast cosmesis improved using the specific ADM fenestration patterns described in the study (and described herein). Specifically, there is improved lower pole expansion, projection, and shape even during the expansion process with the fenestrated allograft positioned as an inferior-lateral sling. In the study, a statistically significant increase was observed in intra-operative fill volume, which resulted in a decreased number of office expansions and faster time to complete fill. Additionally, subjectively less discomfort for the patient was noted with the subsequent intra-office expander fills. Although the fill volume per intra-office expansion event and time until implant exchange did not reach statistical significance in the study, a trend highlighting increased volume per office fill event and a shorter time period to completion of reconstruction with implant exchange was noted. Additionally, due to the improved cosmetic outcomes, even during tissue expansion, tissue expander to implant exchanges were easier and faster, requiring less revisions during the second stage. Furthermore, this was accomplished with a single drain placed in the subcutaneous pocket compared to the previous need for two drains (one subcutaneous and one sub-allograft) for non-fenestrated allograft breast reconstructions to adequately evacuate the reconstructed area.

The large, strategically designed fenestrations used in the study (and described herein) lead to increased vascularization and incorporation of the allograft. During tissue expander removal and implant placement, the fenestrations were easily detected and the ADM was firmly adhered to, and fully integrated with, the patient's native tissue. The fenestrations of some embodiments may increase opportunity for full contact of the ADM to the mastectomy skin flaps, which promotes ADM integration. In the patient population studied, there were no issues with ADM folding or ADM loss, which can be largely attributed to the improved ADM-flap effacement. Additionally, there appeared to be less "knuckling" of underfilled tissue expanders, which not only decreased pressure on the mastectomy skin flaps, thereby preventing extrusion, but also limited pain and patient concerns regarding the under-filled tissue expanders at the site of "knuckling".

Post-operative fluid collection was observed in one patient in this study, however it was not clinically significant and did not require drainage. There were zero patients in the fenestrated ADM group with clinically significant seromas. This low rate was likely due to routine placement of a single round subcutaneous drain in each mastectomy site. Drains were discontinued when drain output had decreased to less than 20 cc of fluid over a 24-hour period. The need for only limited muscular and fascial dissection and the presence of the strategically designed fenestrations with appropriate overlap allows for proper egress of fluid from the tissue expander pocket into the subcutaneous space, which moderates the risk of seroma formation. The ability to only use one drain increases patient comfort and decreases scarring.

Four patients who had major complications had a history of post-operative radiation therapy while the tissue expander was in place. Ideally, expansion was continued post-operatively with the goal of completion prior to the start of radiation. At the initiation of radiation therapy, expansion was held or postponed and mastectomy flaps were monitored routinely. If the patient experienced any significant skin changes or discomfort, saline was removed from the expanders. Radiation and tobacco exposure are both independently associated with an increased risk of complications for breast reconstruction using allograft material[2,4]. Additionally, known complications of radiation therapy include poor wound healing due to decreased tissue vascularity, a thinned epidermis and dermis and poor tissue strength. All of these factors can lead to an increased rate of infection of implanted materials. A previous study by Krueger et al. showed a 37% failure rate with tissue expander/implant reconstructions with post-operative radiation compared to an 8% failure rate for non-irradiated breasts[1].

The improved technique used in this study led to improved intra-operative fill volume, decreased number of post-operative expansions, and improved expansion rate with subjectively less pain and time to full expansion. Patients appeared to benefit from improved cosmetic outcomes with better shape, maintenance of the breast footprint and enhanced comfort due to the decreased number of intra-office fill events and increased intra-operative expansion.

CONCLUSION

It should be understood that although the present disclosure has been specifically disclosed by preferred embodiments and optional features, modification, improvement and variation of the disclosure embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Baxter, Richard A. Acellular Dermal Matrices in Breast Surgery. Clinics in Plastic Surgery. 2012; 39(2).
2. Brooke, S, Mesa M, Uluer M, Michelotti B, Moyer K, Neves R, Mackay D, Potochny J. Complications in Tissue Expander Breast Reconstruction: A comparison of AlloDerm, DermaMatrix, and Flex HD Acellular Inferior Pole Dermal Slings Annals of Plastic Surgery. 2012; 69(4): 347-349.
3. Spear S, Sher S R, Al-Attar, A. Focus on Techniques: Supporting the Soft-Tissue Envelope in Breast Reconstruction. PRS. 2012; 130(5S-2):895-945.
4. Nahabedian, M Y. Acellular Dermal Matrices in Primary Breast Reconstruction: Principles, Concepts, and Indications. PRS. 2012; 130(5S-2):445-53S.

5. McCarthy C M, Lee C N, Halvorson E G, Ridel E, Pusic A L, Mehrara B J, Disa J J. The Use of Acellular Dermal Matrices in Two-Stage Expander/Implant Reconstruction: A Multicenter, Blinded, Randomized Controlled Trial. PRS. 2012; 130(5S-2):57S-67S.
6. Kim, John Y S et al. A Meta-Analysis of Human Acellular Dermia and Submuscular Tissue Expander Breast Reconstruction. PRS. 2012; 129(1):28-41.
7. Nahabedian, M Y. AlloDerm Performance in the Setting of Prosthetic Breast Surgery, Infection, and Irradiation. PRS. 2009; 124(6):1743-53.
8. Namnoum, J D. Expander/Implant Reconstruction with Alloderm: Recent Experience. PRS. 2009; 124(2):387-94.
9. Chun Y S, Verma K, Rosen H. Implant-Based Breast Reconstruction Using Acellular Dermal Matrix and the Risk of Postoperative Complications. PRS. 2010; 125(2): 429-36.
10. Jansen L A, Macadam S A. The use of AlloDerm in postmastectomy alloplastic breast reconstruction: part I. A systematic review. Plast Reconstr Surg, 2011, 127(6), 2232-44.
11. Corp. L, *AlloDerm: Regenerative Tissue Matrix. Life Cell Product Information* 2004, Branchburg, N J: Life Cell Corp.
12. Topol B M, Dalton E F, Ponn T, Campbell C J. Immediate single-stage breast reconstruction using implants and human acellular dermal tissue matrix with adjustment of the lower pole of the breast to reduce unwanted lift. Ann Plast Surg, 2008, 61(5), 494-9.
13. Salzberg C A. Nonexpansive immediate breast reconstruction using human acellular tissue matrix graft (Allo-Derm). Ann Plast Surg, 2006, 57(1), 1-5.
14. Namnoum J D. Expander/implant reconstruction with AlloDerm: recent experience. Plast Reconstr Surg, 2009, 124(2), 387-94.
15. Breuing K H, Colwell A S. Inferolateral AlloDerm hammock for implant coverage in breast reconstruction. Ann Plast Surg, 2007, 59(3), 250-5.
16. Spear S L, Parikh P M, Reisin E, Menon N G. Acellular dermis-assisted breast reconstruction. Aesthetic Plast Surg, 2008, 32(3), 418-25.
17. Glasberg S B, Light D. AlloDerm and Strattice in breast reconstruction: a comparison and techniques for optimizing outcomes. Plast Reconstr Surg, 2012, 129(6), 1223-33.
18. Parikh P M S S, Menon N, Reisin E. Immediate breast reconstruction with tissue expanders and AlloDerm (Abstract). Plast Reconstr Surg, 2006, 11818.
19. Preminger B A, McCarthy C M, Hu Q Y, Mehrara B J, Disa J J. The influence of AlloDerm on expander dynamics and complications in the setting of immediate tissue expander/implant reconstruction: a matched-cohort study Ann Plast Surg, 2008, 60(5), 510-3.
20. Breuing K H, Warren S M. Immediate bilateral breast reconstruction with implants and inferolateral AlloDerm slings. Ann Plast Surg, 2005, 55(3), 232-9.
21. Gamboa-Bobadilla G M. Implant breast reconstruction using acellular dermal matrix. Ann Plast Surg, 2006, 56(1), 22-5.
22. Zienowicz R J, Karacaoglu E. Implant-based breast reconstruction with allograft. Plast Reconstr Surg, 2007, 120(2), 373-81.
23. Becker S, Saint-Cyr M, Wong C, Dauwe P, Nagarkar P, Thornton J F, Peng Y. AlloDerm versus DermaMatrix in immediate expander-based breast reconstruction: a preliminary comparison of complication profiles and material compliance. Plast Reconstr Surg, 2009, 123(1), 1-6; discussion 107-8.
24. Antony A K, McCarthy C M, Cordeiro P G, Mehrara B J, Pusic A L, Teo E H, Arriaga A F, Disa J J. Acellular human dermis implantation in 153 immediate two-stage tissue expander breast reconstructions: determining the incidence and significant predictors of complications. Plast Reconstr Surg, 2010, 125(6), 1606-14.
25. Chun Y S, Verma K, Rosen H, Lipsitz S, Morris D, Kenney P, Eriksson E. Implant-based breast reconstruction using acellular dermal matrix and the risk of postoperative complications. Plast Reconstr Surg, 2010, 125 (2), 429-36.
26. Lanier S T, Wang E D, Chen J J, Arora B P, Katz S M, Gelfand M A, Khan S U, Dagum A B, Bui D T. The effect of acellular dermal matrix use on complication rates in tissue expander/implant breast reconstruction. Ann Plast Surg, 2010, 64(5), 674-8.
27. Sbitany H, Serletti J M. Acellular dermis-assisted prosthetic breast reconstruction: a systematic and critical review of efficacy and associated morbidity. Plast Reconstr Surg, 2011, 128(6), 1162-9.
28. Tanner J C, Jr., Vandeput J, Olley J F. The Mesh Skin Graft. Plast Reconstr Surg, 1964, 34287-92.
29. Vandeput J J, Tanner J C, Boswick J. Implementation of parameters in the expansion ratio of mesh skin grafts. Plast Reconstr Surg, 1997, 100(3), 653-6.
30. Liu A S, Kao H K, Reish R G, Hergrueter C A, May J W, Jr., Guo L. Postoperative complications in prosthesis-based breast reconstruction using acellular dermal matrix. Plast Reconstr Surg, 2011, 127(5), 1755-62.
31. Parks J R, Hammond S E, Walsh W W, Adams R L, Chandler R G, Luce E A. Human Acellular Dermis (ACD) vs. No-ACD in Tissue Expansion Breast Reconstruction. Plast Reconstr Surg, 2012.

What is claimed is:

1. A tissue graft for reconstruction of a breast, the tissue graft comprising:
a plurality of rows of fenestrations formed therein, the plurality of rows of fenestrations comprising:
a first row of fenestrations aligned along a first axis; and
a second row of fenestrations aligned along a second axis;
wherein each first row fenestration within the first row of fenestrations has a length measured along the first axis and within a first range of lengths from a first smallest minimum length to a first largest maximum length and each second row fenestration within the second row of fenestrations has a length measured along the second axis and within a second range of lengths from a second smallest minimum length to a second largest maximum length that does not include any of the first range of lengths; and
wherein the first row of fenestrations is substantially parallel to, and laterally offset from, the second row of fenestrations.

2. The tissue graft of claim 1, wherein 20-90% of a length of a first row fenestration overlaps one or more second row fenestrations.

3. The tissue graft of claim 1, wherein 20-90% of a length of a second row fenestration overlaps one or more first row fenestrations.

4. The tissue graft of claim 1, wherein the plurality of rows further comprises one or more additional rows of fenestrations formed within the tissue graft.

5. The tissue graft of claim 4, wherein the plurality of rows consists of three rows of fenestrations.

6. The tissue graft of claim 4, wherein the plurality of rows consists of four rows of fenestrations.

7. The tissue graft of claim 1, wherein the plurality of rows are equally spaced along an entire width of the tissue graft.

8. The tissue graft of claim 7, wherein the first range of lengths is 1.8-2.3 cm.

9. The tissue graft of claim 7, wherein the second range of lengths is 3-4 cm.

10. The tissue graft of claim 1, wherein the plurality of rows are concentrated within a caudal half of the tissue graft.

11. The tissue graft of claim 1, wherein the plurality of rows are equally spaced along a caudal half of the tissue graft.

12. The tissue graft of claim 11, wherein the first range of lengths is 1.8-2.3 cm.

13. The tissue graft of claim 11, wherein the second range of lengths is 3.0-4.0 cm.

14. The tissue graft of claim 1, wherein the graft is an autograft, allograft, xenograft, engineered graft or synthetic graft.

15. The tissue graft of claim 1, wherein the graft comprises an acellular dermal matrix.

16. The tissue graft of claim 1, wherein the first and second rows of fenestrations are substantially parallel to a cephalic or caudal perimeter of the tissue graft.

17. The tissue graft of claim 1, further comprising a plurality of alignment perforations positioned along a perimeter of the tissue graft, each of the plurality of alignment perforations being a hole;
wherein each of the plurality of fenestrations is an elongated slit; and
wherein each of the plurality of rows of fenestrations is spaced from the perimeter.

18. A tissue graft for reconstruction of a breast, the tissue graft configured to achieve desired expansion of the breast's inferior pole following attachment to a chest wall, wherein the tissue graft comprises:
a plurality of fenestrations disposed therein, the plurality of fenestrations comprising a first row of fenestrations aligned along a first axis and a second row of fenestrations aligned along a second axis, each first row fenestration within the first row of fenestrations having a length measured along the first axis and within a first range of lengths from a first smallest minimum length to a first largest maximum length and each second row fenestration within the second row of fenestrations having a length measured along the second axis and within a second range of lengths from a second smallest minimum length to a second largest maximum length that does not include any of the first range of lengths,
the plurality of fenestrations causing a decrease in an effective Young's modulus of the tissue graft, and consequently yielding a larger deflection profile in accordance with the following equation:

$$\begin{cases} -\partial_y(\sigma \partial_y u) = f, & y \in (0, l), \\ u(0) = 0, \\ u(l) = 0, \end{cases} ;$$

and
a plurality of alignment perforations positioned along a perimeter of the tissue graft, each of the plurality of alignment perforations being a hole;
wherein each of the plurality of fenestrations is an elongated slit and spaced from the perimeter; and
wherein u denotes a deflection profile of the tissue graft from an unstressed state, σ denotes the effective Young's Modulus, f denotes a load stemming from a breast implant positioned against the chest wall, y denotes a distance from the chest wall in a posteroanterior direction, and l denotes a distance from a suture point on the chest wall to a point of attachment at a pectoralis major muscle.

19. The tissue graft of claim 18, wherein upon implantation, the plurality of fenestrations are positioned perpendicular to a posteroanterior line extending directly off a chest wall or parallel to the chest wall.

20. The tissue graft of claim 18, wherein the plurality of fenestrations are positioned within a plurality of rows, and the rows are equally spaced along an entire width of the tissue graft.

21. A tissue graft for reconstruction of a breast, the tissue graft configured to achieve desired expansion of the breast's inferior pole following attachment to a chest wall, wherein the tissue graft comprises:
a plurality of fenestrations disposed therein, the plurality of fenestrations comprising a first row of fenestrations aligned along a first axis and a second row of fenestrations aligned along a second axis, each first row fenestration within the first row of fenestrations having a length measured along the first axis and within a first range of lengths from a first smallest minimum length to a first largest maximum length and each second row fenestration within the second row of fenestrations having a length measured along the second axis and within a second range of lengths from a second smallest minimum length to a second largest maximum length that does not include any of the first range of lengths,
the plurality of fenestrations concentrated in a cephalic portion or caudal portion of the tissue graft such that the tissue graft has an inhomogeneous Young's modulus profile in accordance with the following equation:

$\sigma(y) = a + (1-a)[1 + \tan h(10(x-0.5))]/2;$ and
a plurality of alignment perforations positioned along a perimeter of the tissue graft, each of the plurality of alignment perforations being a hole;
wherein each of the plurality of fenestrations is an elongated slit and spaced from the perimeter; and
wherein σ(y) denotes a local effective Young's modulus profile across a length y of the tissue graft, a represents a targeted effective Young's modulus of the fenestrated portion of the tissue graft, h denotes a width of the tissue graft along which fenestrations are disposed, and x denotes a location along h.

* * * * *